(12) United States Patent
Walter

(10) Patent No.: US 11,944,433 B2
(45) Date of Patent: Apr. 2, 2024

(54) DETECTING AN ANALYTE IN A BODY FLUID

(71) Applicant: Roche Diabetes Care, Inc., Indianapolis, IN (US)

(72) Inventor: Helmut Walter, Heppenheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 18/228,754

(22) Filed: Aug. 1, 2023

(65) Prior Publication Data

US 2023/0371861 A1    Nov. 23, 2023

Related U.S. Application Data

(63) Continuation of application No. 16/068,743, filed as application No. PCT/EP2017/052387 on Feb. 3, 2017, now Pat. No. 11,759,133.

(30) Foreign Application Priority Data

Feb. 5, 2016  (EP) ..................................... 16154469

(51) Int. Cl.
*A61B 5/145*       (2006.01)
*A61B 5/00*        (2006.01)
(Continued)

(52) U.S. Cl.
CPC ...... *A61B 5/14865* (2013.01); *A61B 5/14503* (2013.01); *A61B 5/14532* (2013.01);
(Continued)

(58) Field of Classification Search
CPC ........ A61B 2560/063; A61B 2562/166; A61B 2562/242; A61B 5/14503; A61B 5/14532;
(Continued)

(56) References Cited

U.S. PATENT DOCUMENTS 5,413,690 A   5/1995  Kost et al.
5,762,770 A   6/1998  Pritchard et al.
(Continued)

FOREIGN PATENT DOCUMENTS

CN     1703254     11/2005
CN     101596104   12/2009
(Continued)

OTHER PUBLICATIONS

Amendment in U.S. Appl. No. 16/069,016 dated Jul. 29, 2022.
(Continued)

*Primary Examiner* — Eric J Messersmith
(74) *Attorney, Agent, or Firm* — Woodard, Emhardt, Henry, Reeves & Wagner, LLP

(57) ABSTRACT

A medical device for detecting at least one analyte in a body fluid, a method for assembling the medical device and a method of using the medical device are disclosed. The medical device comprises:
 an analyte sensor having an insertable portion;
 an insertion cannula receiving the insertable portion of the analyte sensor;
 an electronics unit connected with the analyte sensor; and
 a housing comprising an electronics compartment receiving the electronics unit and a sensor compartment receiving the analyte sensor,
 the sensor compartment forming a sealed compartment receiving the insertable portion of the analyte sensor,
 the sealed compartment comprising detachable upper and lower caps,
 the lower cap configured for detachment before insertion,
 the insertion cannula being attached to the upper cap, wherein detaching the upper cap after insertion removes the insertion cannula,
(Continued)

Figure 1:
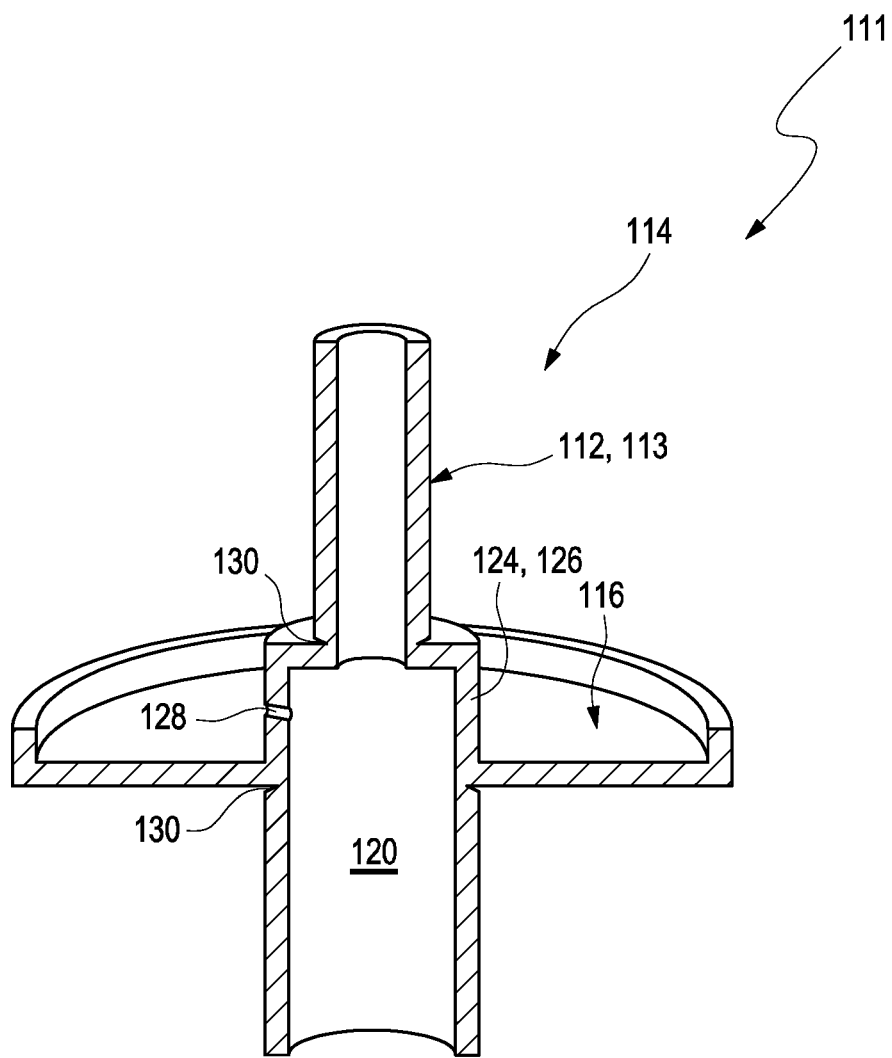
Figure 1:
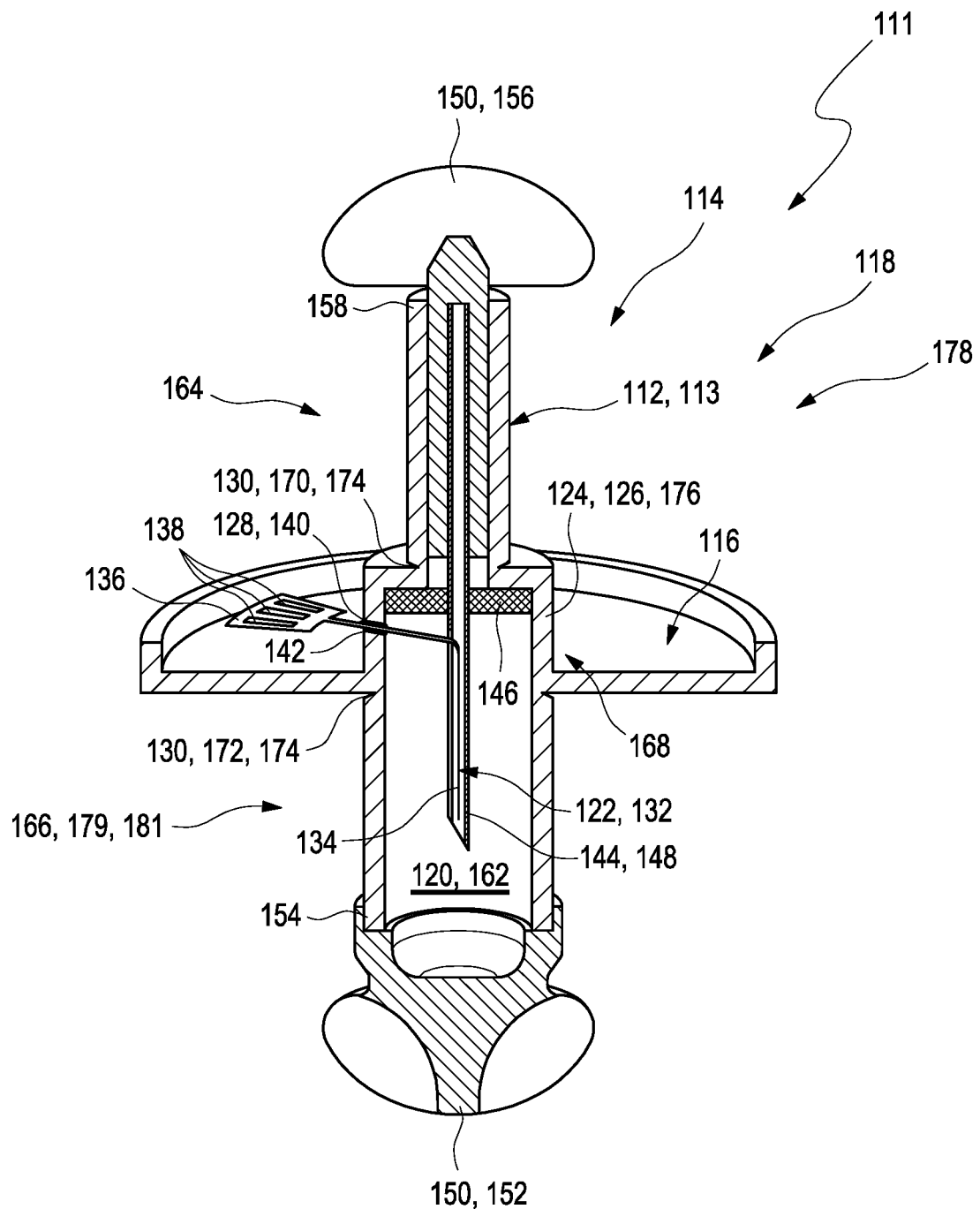
Figure 1:
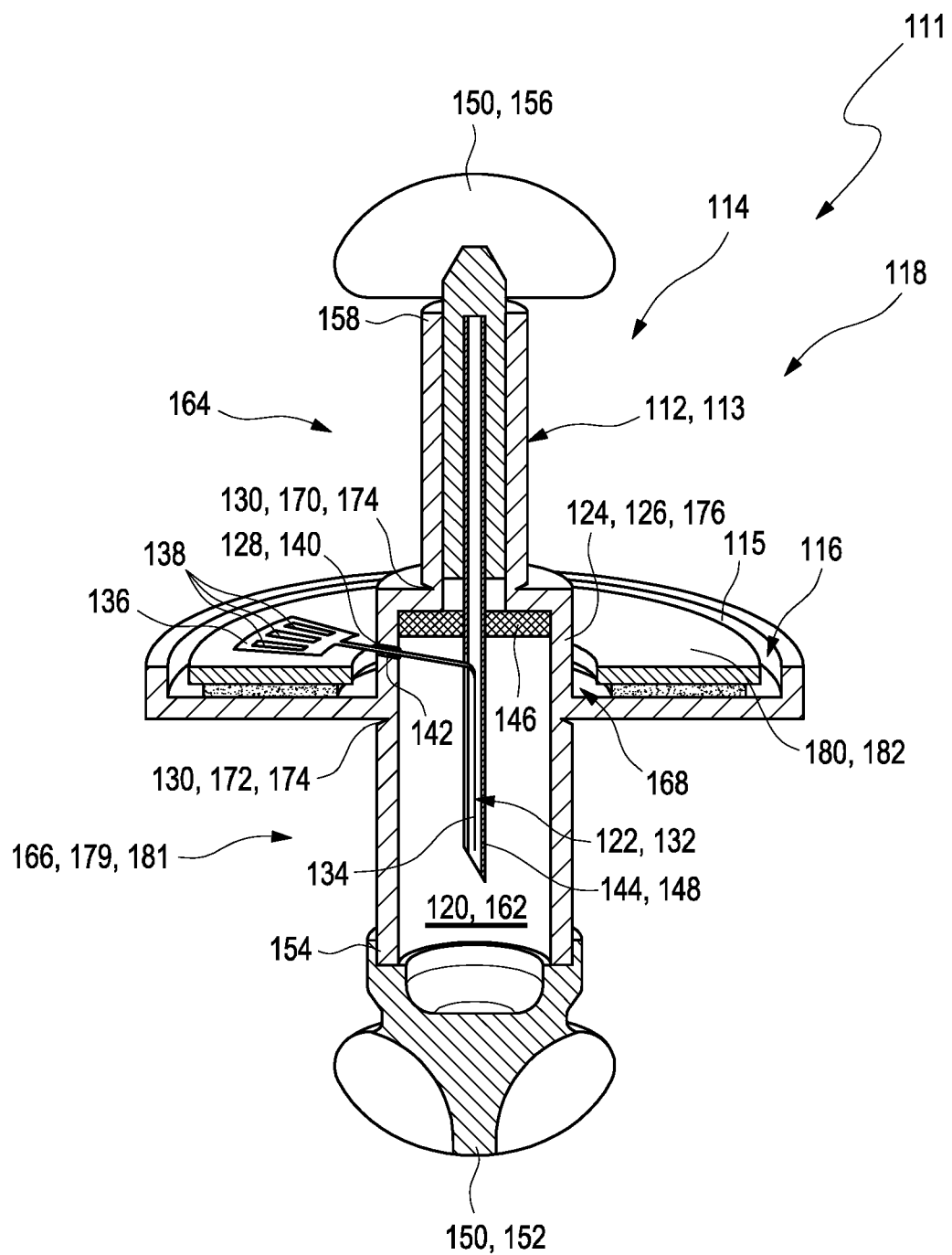
Figure 1:
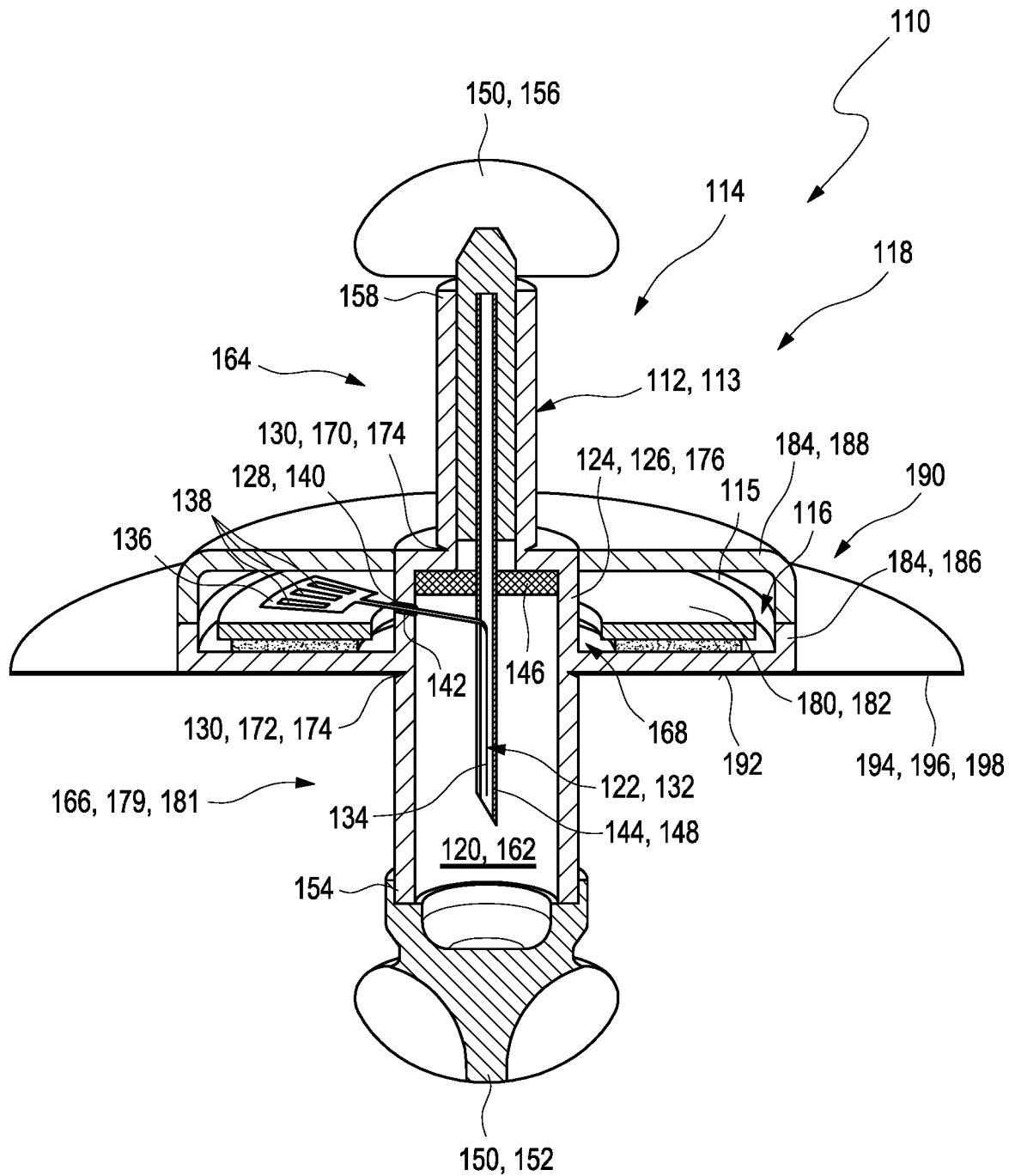

wherein the electronics compartment at least partially surrounds the sensor compartment.

27 Claims, 13 Drawing Sheets

(51) Int. Cl.
  *A61B 5/1486* (2006.01)
  *A61B 5/15* (2006.01)
(52) U.S. Cl.
  CPC ...... *A61B 5/150969* (2013.01); *A61B 5/6849* (2013.01); *A61B 5/150022* (2013.01); *A61B 2560/063* (2013.01); *A61B 2562/166* (2013.01); *A61B 2562/242* (2013.01)
(58) Field of Classification Search
  CPC .......... A61B 5/14865; A61B 5/150022; A61B 5/150969; A61B 5/6849
  See application file for complete search history.

(56) References Cited

U.S. PATENT DOCUMENTS

| | | |
|---|---|---|
| 5,798,031 A | 8/1998 | Charlton et al. |
| 6,129,823 A | 10/2000 | Hughes et al. |
| 6,256,523 B1 | 7/2001 | Diab et al. |
| 6,360,888 B1 | 3/2002 | McIvor et al. |
| 8,577,437 B2 | 11/2013 | Roesicke et al. |
| 8,721,544 B2 | 5/2014 | Roesicke et al. |
| 8,764,657 B2 | 7/2014 | Curry et al. |
| 9,164,056 B2 | 10/2015 | Harrison et al. |
| 9,693,713 B2 * | 7/2017 | Pace ................ A61B 5/150358 |
| 2005/0012731 A1 | 1/2005 | Yamazaki et al. |
| 2005/0013731 A1 | 1/2005 | Burke et al. |
| 2005/0101912 A1 | 5/2005 | Faust et al. |
| 2005/0158205 A1 | 7/2005 | Swanson et al. |
| 2005/0283114 A1 | 12/2005 | Bresina et al. |
| 2006/0020186 A1 | 1/2006 | Brister et al. |
| 2007/0073129 A1 | 3/2007 | Shah et al. |
| 2007/0189928 A1 | 8/2007 | Sabol |
| 2007/0202488 A1 | 8/2007 | Hendrix et al. |
| 2008/0027296 A1 | 1/2008 | Hadvary et al. |
| 2008/0097246 A1* | 4/2008 | Stafford ................ G16H 40/63 600/584 |
| 2008/0190766 A1 | 8/2008 | Rush et al. |
| 2008/0234561 A1 | 9/2008 | Roesicke et al. |
| 2008/0242962 A1 | 10/2008 | Roesicke et al. |
| 2008/0255440 A1 | 10/2008 | Ellerson et al. |
| 2008/0319278 A1 | 12/2008 | Omtvelt et al. |
| 2009/0105569 A1 | 4/2009 | Stafford |
| 2010/0049014 A1 | 2/2010 | Funderburk et al. |
| 2010/0200538 A1 | 8/2010 | Petisce et al. |
| 2010/0286714 A1 | 11/2010 | Gyrn et al. |
| 2010/0324392 A1 | 12/2010 | Yee et al. |
| 2010/0331738 A1 | 12/2010 | Stein et al. |
| 2011/0288574 A1 | 11/2011 | Curry et al. |
| 2012/0053608 A1 | 3/2012 | Shoshihara et al. |
| 2012/0083673 A1 | 4/2012 | Al-Ali et al. |
| 2012/0116190 A1 | 5/2012 | Iketani et al. |
| 2012/0190952 A1 | 7/2012 | Stafford |
| 2012/0197222 A1 | 8/2012 | Donnay et al. |
| 2012/0215083 A1 | 8/2012 | Shoshihara et al. |
| 2012/0259192 A1 | 10/2012 | Tsukada et al. |
| 2013/0018454 A1 | 1/2013 | Lelkes et al. |
| 2013/0150691 A1 | 6/2013 | Pace et al. |
| 2013/0184541 A1 | 7/2013 | Antonio et al. |
| 2013/0267813 A1 | 10/2013 | Pryor et al. |
| 2013/0313130 A1 | 11/2013 | Little et al. |
| 2014/0066730 A1 | 3/2014 | Roesicke et al. |
| 2015/0018643 A1 | 1/2015 | Cole et al. |
| 2015/0080684 A1 | 3/2015 | Frey et al. |
| 2016/0022179 A1 | 1/2016 | Di Resta et al. |
| 2016/0058471 A1 | 3/2016 | Peterson et al. |
| 2016/0287150 A1 | 10/2016 | Yu |
| 2016/0331284 A1 | 11/2016 | Pace |
| 2017/0202488 A1 | 7/2017 | Stafford |
| 2017/0202497 A1 | 7/2017 | Yee et al. |
| 2017/0251922 A1 | 9/2017 | Roesicke et al. |
| 2018/0325433 A1 | 11/2018 | Prais et al. |
| 2018/0360358 A1 | 12/2018 | Baker et al. |
| 2018/0360493 A1 | 12/2018 | Baker et al. |
| 2019/0151564 A1 | 5/2019 | Schrul et al. |
| 2019/0231238 A1 | 8/2019 | Frey et al. |

FOREIGN PATENT DOCUMENTS

| | | |
|---|---|---|
| CN | 102245236 | 11/2011 |
| CN | 102387746 | 3/2012 |
| CN | 102469967 | 5/2012 |
| CN | 103156619 | 6/2013 |
| CN | 104470422 | 3/2015 |
| CN | 204233136 | 4/2015 |
| CN | 204233137 | 4/2015 |
| CN | 104780835 | 7/2015 |
| CN | 105534508 | 5/2016 |
| DE | 954712 | 12/1956 |
| DE | 20020566 | 1/2002 |
| EP | 1475113 | 11/2004 |
| EP | 1929941 | 6/2008 |
| EP | 1972269 | 9/2008 |
| EP | 1972269 A1 | 9/2008 |
| EP | 2163190 | 3/2010 |
| EP | 2919000 | 9/2015 |
| EP | 2982303 | 2/2016 |
| EP | 14180045.8 | 2/2016 |
| EP | 3202323 | 8/2017 |
| JP | 2004049607 | 2/2004 |
| JP | 2004229674 | 8/2004 |
| JP | 2008522786 | 7/2008 |
| JP | 2009525794 | 7/2009 |
| JP | 2012071109 | 4/2012 |
| JP | 2013523216 | 6/2013 |
| JP | 2014144025 | 8/2014 |
| JP | 2015515305 | 5/2015 |
| KR | 101393856 | 8/2012 |
| RU | 133942 U1 | 10/2013 |
| WO | WO 2006/015922 | 2/2006 |
| WO | WO 2010/091005 | 8/2010 |
| WO | WO 2011/119896 | 9/2011 |
| WO | WO 2011119896 A1 | 9/2011 |
| WO | WO 2011/121023 | 10/2011 |
| WO | WO 2011/037030 | 2/2013 |
| WO | WO 2013/090215 | 6/2013 |
| WO | WO 2013/144255 | 10/2013 |
| WO | WO 2014/018928 A1 | 1/2014 |
| WO | WO 2014/179343 | 11/2014 |
| WO | WO 2016/012482 | 1/2016 |
| WO | WO 2016/012497 | 1/2016 |
| WO | WO 2016/036924 | 3/2016 |
| WO | WO 2017/019224 | 2/2017 |
| WO | WO 2017/037191 | 3/2017 |
| WO | WO 2017/116915 | 7/2017 |
| WO | WO 2018/195286 | 10/2018 |
| WO | WO 2018/215421 | 11/2018 |
| WO | WO 2018/222010 | 12/2018 |

OTHER PUBLICATIONS

Office Action in U.S. Appl. No. 16/069,016 dated Aug. 20, 2020.
Office Action in U.S. Appl. No. 16/069,016 dated Jan. 12, 2022.
Office Action in U.S. Appl. No. 16/069,016 dated Jan. 29, 2021.
Office Action in U.S. Appl. No. 16/069,016 dated Sep. 7, 2021.
Office Action in U.S. Appl. No. 16/898,049 dated May 10, 2022.
Response to Office Action in U.S. Appl. No. 16/069,016 dated Apr. 14, 2021.
Response to Office Action in U.S. Appl. No. 16/069,016 dated Jul. 12, 2022.
Response to Office Action in U.S. Appl. No. 16/069,016 dated Nov. 2, 2021.

(56) References Cited

OTHER PUBLICATIONS

Response to Office Action In U.S. Appl. No. 16/069,016 dated Nov. 20, 2020.
Office Action in U.S. Appl. No. 18/228,283 dated Sep. 26, 2023.

* cited by examiner

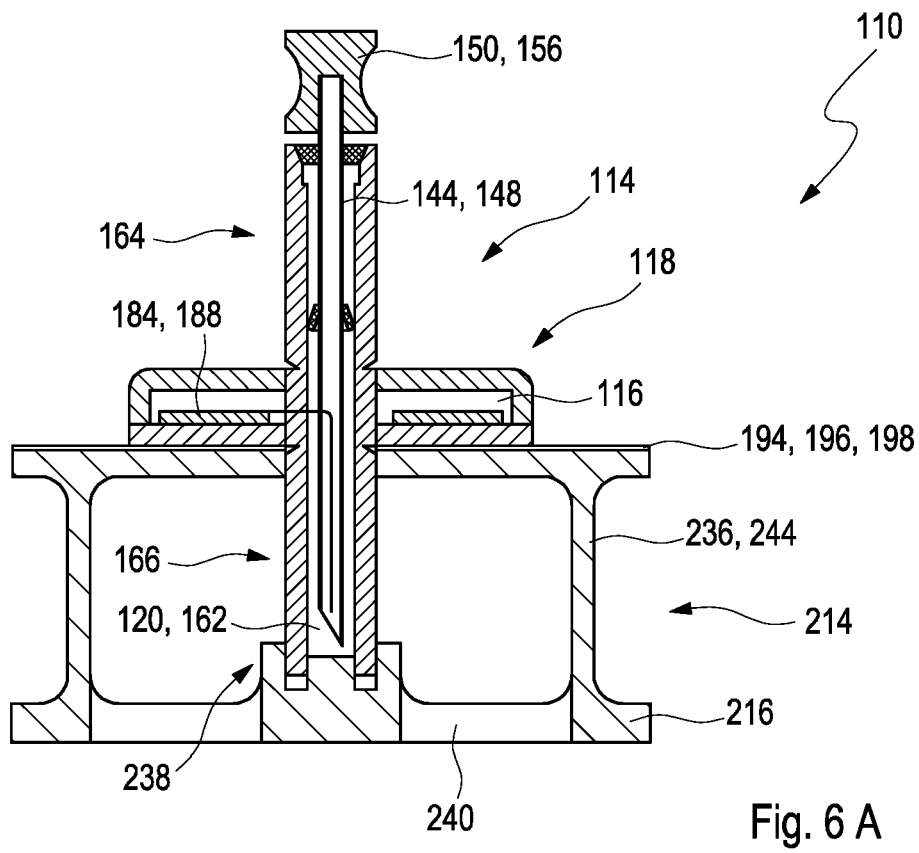
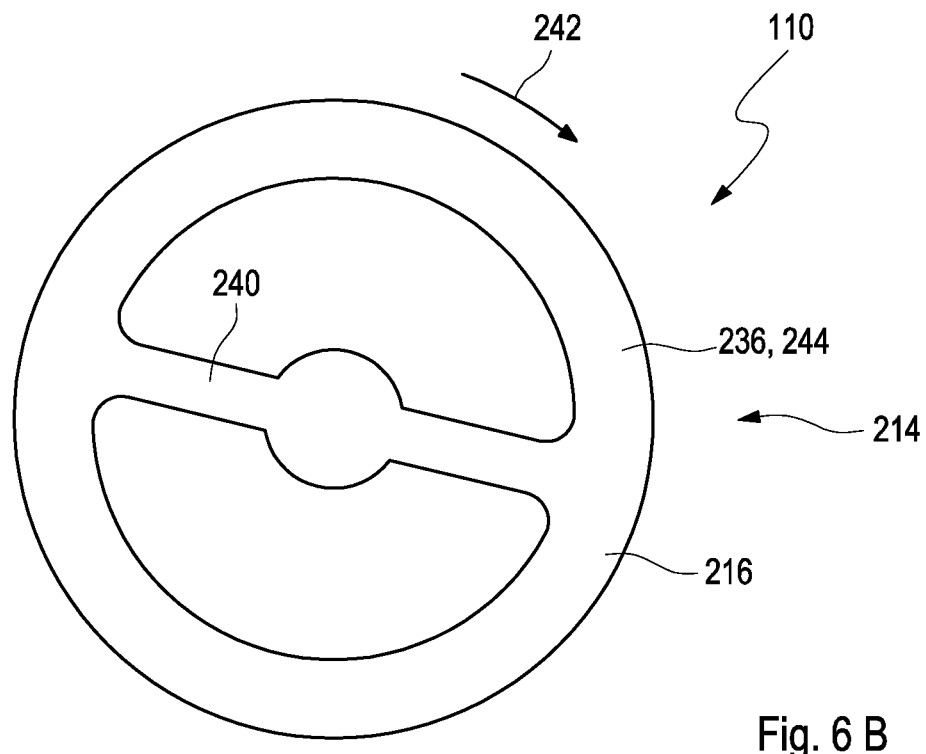

DETECTING AN ANALYTE IN A BODY FLUID

FIELD OF THE INVENTION

The invention relates to a medical device for detecting at least one analyte in a body fluid, a method for assembling a medical device and a method of using a medical device. The device and methods according to the present invention may mainly be used for long-term monitoring of an analyte concertation in a body fluid, such as for long-term monitoring of a blood glucose level or of the concentration of one or more other types of analytes in a body fluid. The invention may both be applied in the field of home care as well as in the filed of professional care, such as in hospitals. Other applications are feasible.

RELATED ART

Monitoring certain body functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown e.g. in DE 954712 B. Other techniques or providing electrical contacts, such as by appropriate spring contacts, are generally known and may be applied.

In order to avoid detrimental effects of the aggressive environment onto the conductive properties of the electrical contact, the region of the electrical contact is typically encapsulated and protected against humidity. Generally, encapsulations of electrical locks and contacts by using appropriate seals is known from e.g. DE 200 20 566 U1. Specifically in transcutaneous or subcutaneous sensors, in which the region of electrical contact between the sensor and the control part is close to the human skin, an efficient protection against humidity, dirt, sweat and detergents, such as detergents used for body care, is crucial.

US2012/0197222 A1 discloses medical device inserters and processes of inserting and using medical devices. A method is disclosed which comprises removing a substantially cylindrical cap from an inserter to expose a substantially cylindrical sleeve; removing a cover from a substantially cylindrical container holding sensor components; and fitting the sensor components into the inserter.

WO 2010/091028 A1 discloses an integrated analyte monitoring device assembly. The integrated analyte monitoring device assembly comprises an analyte sensor for transcutaneous positioning through a skin layer and maintained in fluid contact with an interstitial fluid under the skin layer during a predetermined time period. The analyte sensor has a proximal portion and a distal portion. Sensor electronics are coupled to the analyte sensor. The sensor electronics comprises a circuit board having a conductive layer and a sensor antenna disposed on the conductive layer. Further, the sensor electronic comprises one or more electrical contacts provided on the circuit board and coupled with the proximal portion of the analyte sensor to maintain continuous electrical communication. Further, the sensor electronic comprises: a data processing component provided on the circuit board and in signal communication with the analyte sensor. The data processing component is configured to execute one or more routines for processing signals received from the analyte sensor. Further, the data processing component is configured to control the transmission of data associated with the processed signals received from the analyte sensor to a remote location using the sensor antenna in response to a request signal received from the remote location.

WO 2014/018928 A1 discloses on-body analyte monitoring devices configured for uncompressed and compressed configurations and methods of using the analyte monitoring devices. The devices comprise a collapsible housing, wherein upon desired placement and user application of force to the housing converts the analyte monitoring device from an uncompressed configuration to a low-profile compressed state while guiding an analyte sensor through the skin and into contact with bodily fluid to measure and analyte level therein. Also provided are systems and kits.

European patent application number 14 180 045.8, filed on Aug. 6, 2014, discloses a medical device and a method for producing a medical device. The medical device comprises at least one implantable device having at least one implantable portion adapted for at least partially being implanted into a body tissue of a user. The implantable device further having at least one contact portion connected to the implantable portion. The medical device further comprises at least one housing. The housing is configured to receive the implantable portion. The housing is configured to provide a sterile packaging such that the implantable portion is sealed against a surrounding environment. The housing comprises at least one first part and at least one second part. The first part and the second part are removable connectable to form the sterile packaging. The first part comprises at least one first sealing surface and the second part comprises at least one second sealing surface. The first sealing surface and the second sealing surface interact to form a sealing area. The implantable device has an interconnecting portion connecting the implantable portion and the contact portion. The interconnecting portion is led through the sealing area.

Despite the advantages and the progress achieved by the above-mentioned developments, specifically in the field of continuous monitoring technology, some significant technical challenges remain. Thus, generally, known techniques for protecting and electrical contact between a sensor and a control part generally are rather complex. An assembly of a plurality of components is generally required, which typically implies a complex and costly manufacturing process. Further, known techniques generally require voluminous components, which is an issue, specifically considering the fact that miniaturizing the sensor systems is a factor contributing to the convenience of use. Specifically in case complex encapsulation parts manufactured by plastic molding techniques are required for protecting the electrical contacts, a rising of costs and sensor volume typically has to be taken into account. Further, cleaning of complex protective covers, such as protections including O-rings or other seals, turns out to be difficult.

Problem to be Solved

It is therefore an objective of the present invention to provide a medical device for detecting at least one analyte in a body fluid, a method for assembling a medical device and a method of using a medical device, which at least partially avoid the shortcomings of known devices and methods of thus kind and which at least partially address the above-mentioned challenges. Specifically, a device and methods shall be disclosed which allow for easy manufacturing and simple handling processes by a user.

SUMMARY OF THE INVENTION

This problem is solved by a medical device for detecting at least one analyte in a body fluid, a method for assembling a medical device and a method of using a medical device, having the features of the independent claims. Preferred embodiments of the invention, which may be realized in an isolated way or in any arbitrary combination, are disclosed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a medical device for detecting at least one analyte in a body fluid is disclosed. The medical device comprises at least one analyte sensor having an insertable portion adapted for at least partially being inserted into a body tissue of a user. The medical device further comprises at least one insertion cannula. The analyte sensor is at least partially placed inside the insertion cannula. Further, the medical device comprises at least one electronics unit. The analyte sensor is operably connected to the electronics unit. Further, the medical device comprises at least one housing. The housing comprises at least one electronics compartment configured to at least partially receive the electronics unit. The housing further comprises at least one sensor compartment configured to at least partially receive the analyte sensor. The sensor compartment forms a sealed compartment receiving at least the insertable portion of the analyte sensor. The sealed compartment comprises at least one detachable upper cap and at least one detachable lower cap. The detachable lower cap is configured for detachment before insertion, thereby opening the insertable portion for insertion. The insertion cannula is attached to the detachable upper cap. The detachable upper cap is configured for detachment after insertion, thereby removing the insertion cannula. The electronics compartment at least partially surrounds the sensor compartment.

As generally used within the present invention, the term "medical device" may refer to an arbitrary device configured for conducting at least one medical analysis and/or at least one medical procedure. The medical device therefore generally may be an arbitrary device configured for performing at least one diagnostic purpose and/or at least one therapeutic purpose. In the following, without restricting further embodiments, the present invention mainly will be described in terms of a medical device configured for performing at least one diagnostic purpose and, specifically, a medical device comprising at least one analyte sensor for performing at least one analysis. The medical device specifically may comprise an assembly of two or more components capable of interacting with each other, such as in order to perform one or more diagnostic and/or therapeutic purposes, such as in order to perform the medical analysis and/or the medical procedure. Specifically, the two or more components may be capable of performing at least one detection of the at least one analyte in the body fluid and/or in order to contribute to the at least one detection of the at least one analyte in the body fluid. The medical device generally may also be or may comprise at least one of a sensor assembly, a sensor system, a sensor kit or a sensor device.

The medical device may be a disposable medical device. The term "disposable medical device" may generally refer to an arbitrary medical device configured to be disposed of after use. Thus, one or more materials may specifically be low priced and/or easily recyclable. Specifically, the electronics unit may be a single-use electronics unit. The term "single-use" may generally refer to a property of an arbitrary element of being configured to be applied only for one time. Thus, after detecting the at least one analyte in the body fluid, the user may remove the electronics units from the body tissue, dispose the electronics unit and may utilize a further, new medical device comprising a further, new electronics unit for another detection of the analyte in the body fluid.

As generally used within the present invention, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

As further used herein, the term "body fluid" generally may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may be an analyte-specific detection.

As further used herein, the term "detect" generally refers to the process of determining the presence and/or the quantity and/or the concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal. As further used herein, the term "determining a concentration" generally may refer to a process of generating at least one representative result or a plurality of representative results indicating the concentration of the analyte in the body fluid.

As further used herein, the term "analyte sensor" may generally refer to an arbitrary element which is adapted to perform the above-mentioned process of the detection and/or which is adapted to be used in the above-mentioned process of the detection. Thus, the sensor specifically may be adapted to determine the concentration of the analyte and/or a presence of the analyte.

The analyte sensor specifically may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The detection may be analyte-specific. The measurement may be a qualitative and/or a quantitative measurement. Still, other embodiments are feasible.

The analyte sensor may particularly be a transcutaneous sensor. As used herein, the term "transcutaneous sensor" generally refers to an arbitrary sensor which is adapted to be fully or at least partly arranged within the body tissue of the patient or the user. For this purpose, the analyte sensor comprises the insertable portion. The term "insertable portion" may generally refer to a part or component of an element configured to be insertable into an arbitrary body tissue. In order to further render the analyte sensor to be usable as a transcutaneous sensor, the analyte sensor may fully or partially provide a biocompatible surface, i.e. a surface which, at least during durations of use, do not have any detrimental effects on the user, the patient or the body tissue. Specifically, the insertable portion of the analyte sensor may have a biocompatible surface. As an example, the transcutaneous sensor, specifically the insertable portion, may fully or partially be covered with at least one biocompatible membrane, such as at least one polymer membrane or gel membrane which is permeable for the at least one analyte and/or the at least one body fluid and which, on the other hand, retains sensor substances such as one or more test chemicals within the sensor and prevents a migration of these substances into the body tissue. Other parts or components of the analyte sensor may stay outside of the body tissue. The other parts may be connectable to an evaluation device such as to the electronics units as will further be described below.

The transcutaneous sensor generally may be dimensioned such that a transcutaneous insertion is feasible, such as by providing a width in a direction perpendicular to an insertion direction of no more than 5 mm, preferably of no more than 2 mm, more preferably of no more than 1.5 mm. The sensor may have a length of less than 50 mm, such as a length of 30 mm or less, e.g. a length of 5 mm to 30 mm. As used herein, the term "length" may refer to a direction parallel to the insertion direction. It shall be noted, however, that other dimensions are feasible.

The term "insertion cannula" may generally refer to an arbitrary element which may be insertable into the body tissue of the user, particularly in order to deliver or to transfer a further element. Therefore, the insertion cannula may specifically be or may comprise a hollow tube or a hollow needle. The insertion cannula e.g. may comprise at least one cross-section selected from the group consisting of: round, elliptical, U shaped, V shaped. Still, other embodiments are feasible. Specifically, the insertion cannula may be a slotted cannula. Alternatively, the insertion cannula may be a non-slotted cannula. The insertion cannula may be configured to be inserted vertically or at an angle of 90° to 30° to the body tissue of the user.

The medical device may further comprise at least one septum received in the sensor compartment. As generally used herein, the term "septum" may generally refer of an arbitrary sealing element configured for sealing of a volume or room providing an environmental protection against moisture and/or an ambient atmosphere, or the like. As an example, the septum may be or may comprise at least one pierceable foil, disk, shim, plug or plate, made of a material which may be pierced by the insertion cannula and which may re-seal a piercing hole generated by the insertion cannula after retraction of the insertion cannula. Specifically, the septum may be made of an elastic material such as an elastomer. The septum may be manufactured may injection molding, specifically by two-component injection molding. The septum may be penetrable by an elongate object with a small diameter such as by the insertion cannula. After a penetration by the elongate object, an opening of the septum caused by the elongate object may be closed itself and the septum may further be configured to provide a tight sealing from the environment of the volume or the room. Specifically, the septum may be configured for sealing a remainder of the sensor compartment after detachment of the detachable upper cap. The insertion cannula may be configured for being pulled through the septum when the detachable upper cap is detached from the housing.

Further, the insertion cannula may comprise at least one barbed hook configured to prevent a further movement of the insertion cannula after usage. As further used herein, the term "barbed hook" may refer to an arbitrary tool which may comprise a portion which is curved or indented such that the portion may be applied to hold another object. Moreover, the barbed hook may be shaped in a specific manner such that a passing of the other object through the barbed hook may only be possible in one direction, wherein, in the counter direction, a movement may be completely suppressed or at least to a large extend reduced. Specifically, this property may be realized by small, further hooks being located such that ends of the hooks may point in a direction opposing a direction in which the other object is movable.

The medical device may further comprise at least one retraction mechanism for retracting the insertion cannula after insertion of the insertable portion of the analyte sensor into the body tissue. The term "retraction mechanism" may generally refer to an arbitrary construction which is configured to move an object in an opposite direction of a direction in which the object may have been moved before the retraction mechanism is applied. Therefore, the retraction mechanism may comprise at least one retraction spring element, more preferably at least one retraction spring element disposed between the housing and the insertion cannula and biased in order to retract the insertion cannula from the body tissue. The retraction mechanism may at least partially be comprised within the detachable upper cap.

As used herein, the term "electronics unit" generally refers to an arbitrary device having at least one electronic component. Specifically, the electronics unit may comprise at least one electronic component for one or more of performing a measurement with the analyte sensor, performing a voltage measurement, performing a current measurement, recording sensor signals, storing measurement signals or measurement data, transmitting sensor signals or measurement data to another device. The electronics unit may specifically be embodied as a transmitter or may comprise a transmitter, for transmitting data. Other embodiments of the electronic components are feasible.

The electronics unit may comprise at least one interconnect device, preferably a printed circuit board, more preferably a flexible printed circuit board. As described above, the analyte sensor is "operably connected" to the electronics unit. The term "operably connected" may specifically refer to a state, wherein two or more objects are connected to each other such that they can interact with each other. Specifically, the analyte sensor may be operably connected to the electronics unit such that sensor signals of the analyte sensor may be transmitted to the electronics unit. Thus, the term "operably connected" may also refer to an electrically conductive connection. The analyte sensor may be electrically connected to the interconnect device, preferably via at least one of a soldering connection, a welding connection, an electrical bonding, a conductive adhesive material or a plug connection. The interconnect device may be fixedly positioned within the electronics compartment of the housing.

As generally used herein, the term "housing" may generally refer to an arbitrary element which is adapted to fully or partially surround and/or receive one or more elements in order to provide one or more of a mechanical protection, a mechanical stability, an environmental protection against moisture and/or ambient atmosphere, a shielding against electromagnetic influences or the like. Thus, the housing may simply provide a basis for attachment and/or holding one or more further components or elements. Additionally or alternatively, the housing may provide one or more interior spaces for receiving one or more further components or elements. The housing may specifically be manufactured by injection molding. However, other embodiments are feasible. Exemplarily, the electronics unit may be sealed or potted as will further be described below.

As used herein, the term "compartment" may generally refer to an arbitrary subpart of a superior element creating a partially or fully enclosed space that may be usable to contain and/or store objects. The subpart may specifically be completely or at least to a large extend closed such that an interior of the compartment may be isolated from a surrounding environment. Exemplarily, the compartment may be separated from other parts of the superior element by one or more walls. Thus, within the housing, two or more compartments may be comprised which may fully or partially be separated from one another by one or more walls of the housing. Each compartment may comprise a continuous space or lumen configured for receiving one or more objects.

As described above, the sensor compartment forms a sealed compartment. The term "sealed compartment" may refer to a property of a compartment of being isolated from a surrounding environment such that a transfer of gas, fluids and/or solid elements is completely or at least to a large extend reduced. Specifically, the sensor compartment may be configured to provide a sterile packaging for the insertable portion of the analyte sensor. Exemplarily, the detachable lower cap may be a sterile cap configured to provide sterile packaging for the insertable portion of the analyte sensor, such that the insertable portion is sealed against a surrounding environment. The term "sterile" may generally refer to a property of an arbitrary object of being at least to a large extend free from all forms of life and/or other biological agents such as prions, viruses, fungi, bacteria or spore forms. Thus, the sterile object may be treated by at least one sterilization process that eliminates and/or deactivates the forms of life and/or the other biological agents. The sterilization process may comprise one or more of the following techniques: heating, chemical treatment, irradiation, high pressure, filtration. However, other techniques are feasible. The sterilization process may be conducted within a specified region or area of the object such as a surface of the object.

The electronics compartment and the sensor compartment may be designed integrally. The term "integrally" may refer to a state wherein two or more components are arranged in a space-saving or compact manner. At least one of the two or more components may be permanently built into at least another one of the two or more components. Further, the two or more components may be designed in a complementary manner such that the components may be able to interact with each other. Exemplarily, the electronics compartment and the sensor compartment may form a single piece. The electronics compartment and the sensor compartment may be at least partially formed by one single housing element. The electronics compartment and the sensor compartment may share a common wall of the housing. The common wall may at least partially be designed as a cylindrical ring surrounding the insertion cannula.

The sensor compartment may comprise at least one intermediate component. The term "intermediate component" may refer to an arbitrary component or compartment between at least two other compartments and/or which may be located in at least one other compartment. Thus, the intermediate component may be located in the sensor compartment and may be sealed from the electronics compartment. The intermediate component may be or may comprise an intermediate compartment or, as an example, a sealing ring or a ring-shaped element. Other embodiments are feasible. The electronics compartment may be connected to the intermediate component. Specifically, the electronics compartment may at least partially surround the intermediate component. The electronics compartment and the intermediate component may share at least one common wall. The intermediate component may form a wall of the electronics compartment. Additionally, the intermediate component may at the same time be part of the sensor compartment. The intermediate component may be at least partially designed as a cylindrical ring surrounding the insertion cannula. The detachable upper cap and the detachable lower cap may be separated by the intermediate component and may both be detachably connected to the intermediate component.

The term "cap" may refer to an arbitrary element which is configured to close or to seal a volume. Specifically, the cap may close or seal an opening of an arbitrary container. The terms "upper cap" and "lower cap" may be considered as description without specifying an order and without excluding a possibility that several kinds of upper caps and lower caps may be applied. The term "detachable" may refer to a property of an element of being removable from an arbitrary object. Thereby, a close bonding or contact between the element and the object may be disconnected. Generally, the element may be removable in a reversible manner wherein the element may be attachable and detachable from the object or in an irreversible manner wherein the element may not be attachable to the object after detachment. Specifically, as will be outlined in further detail below, the detachable upper cap and the detachable lower cap may be connected to the intermediate component via at least one predetermined breaking point, such as via at least one predetermined breaking point having a weakening in the wall of the housing in order to allow for a simple and well-defined detachment of the caps by hand, such as at least one predetermined breaking point comprising one or more groves, notches or slots in the wall.

The detachable upper cap and/or the detachable lower cap may exemplarily have an elongate shape and provide an interior volume. The detachable upper cap and/or the detachable lower cap may have one or more handles allowing for a user to detach the respective cap. The detachable upper cap and the detachable lower cap may be detachably connected to the intermediate component. Specifically, the detachable upper cap and the detachable lower cap may be detachably connected to the intermediate component on opposing sides of the intermediate component. Specifically, the detachable upper cap may partially surround the insertion cannula. The insertion cannula may be fixedly attached to the detachable upper cap.

As outlined above, the detachable upper cap may be detachably connected to the intermediate component at at least one upper predetermined breaking point. The detachable lower cap may be detachably connected to the intermediate component at at least one lower predetermined breaking point. As further used herein, the term "predetermined breaking point" may refer to an arbitrary part of an element being configured to break during mechanical load while other parts of the element remain undamaged. Specifically, the predetermined breaking point may comprise at least one notch wherein a thickness of the element may be smaller in comparison to other parts of the element. The upper predetermined breaking point and the lower predetermined breaking point may specifically be ring-shaped breaking points. The terms "upper breaking point" and "lower breaking point" may be considered as description without specifying an order and without excluding a possibility that several kinds of upper breaking points and lower breaking points may be applied.

The electronics compartment and the sensor compartment may be connected to each other via at least one sealed opening. The term "sealed" may generally refer to a property of an arbitrary element of being completely or at least to a large extend isolated from a surrounding environment. The sealed opening may comprise at least one sealing element. The term "sealing element" may generally refer to an arbitrary element which is configured to cover one or more elements to be sealed off from environmental influences such as moisture. The sealing element may seal the sensor compartment from the electronics compartment. Exemplarily, the sealing element may comprise at least one sealing lip. As used herein, the term "sealing lip" may refer to a maximum in a cross-sectional profile of the sealing element, which, when the sealing element thereon is pressed on another surface, is the first part of the sealing element to contact the other surface. The profile itself may be symmetric or asymmetric in shape, wherein an asymmetric profile may be favorable. The sealing element may comprise at least one sealing material, particularly a deformable sealing material, more preferably an adhesive material. The analyte sensor may pass through the sealed opening. The analyte sensor may be partially received in the electronics compartment and partially received in the sensor compartment. Specifically, the insertable portion may be at least partially received in the sensor compartment.

The electronics compartment may comprise at least two housing portions. The at least two housing portions may comprise at least one lower housing portion and at least one upper housing portion. The terms "lower housing portion" and "upper housing portion" may be considered as description without specifying an order and without excluding a possibility that several kinds of lower housing portions and upper housing portions may be applied.

Exemplarily, the upper housing portion may comprise one or more of a cover of an adhesive sealing material, more preferably at least one elastic material, particularly an elastic polymeric material. The upper housing portion and the lower housing portion may be connected via one or more of a form-fit connection, a force-fit connection or a connection may material engagement, more specifically by a connection using a least one adhesive and/or at least one bonding. The upper housing portion may form an encapsulation for the electronics components of the electronics unit.

The lower housing portion may comprise at least one lower surface configured for being placed on a user's skin. Specifically, the medical device may comprise at least one adhesive surface for attachment to the user's skin. The term "adhesive surface" may refer to a property of an arbitrary surface of being capable to bind to an object and to resist separation. Exemplarily, the adhesive surface may comprise at least one plaster or an adhesive strip. The plaster or the adhesive strip may comprise at least one adhesive material. The adhesive surface may be directly or indirectly attached to the housing. The adhesive surface may be a lower surface of the electronics compartment. The insertable portion of the analyte sensor and the detachable lower cap may extend from a lower surface of the electronics compartment. The term "lower surface" may specifically refer to a surface of the electronics compartment facing the skin user's skin. The adhesive surface may exemplarily have a shape of a circular ring surrounding the analyte sensor.

The detachable upper cap and/or the detachable upper cap may comprise at least one handle. As further used herein, the term "handle" may refer to an arbitrary element which may be part of an object that can be moved or used by hand. Specifically, the detachable lower cap may comprise the handle configured for enabling the user to detach the detachable lower cap from the medical device. The handle may comprise at least one hygroscopic material, preferably at least one desiccant, more preferably activated carbon.

The medical device may further comprise at least one insertion aid configured for enabling a user to drive the insertion cannula into the body tissue and to insert the insertable portion of the analyte sensor. As further used herein, the term "insertion aid" may refer to an arbitrary technical construction being configured to insert an object into another object. Therefore, the insertion aid may comprise at least one insertion mechanism. As further used herein, the term "mechanism" may refer to an arbitrary mechanism designed to transform input forces and movement into a desired set of output forces and movement. Specifically, the insertion mechanism may be configured such that the user may apply a force in a direction of insertion to the insertion cannula. Therefore, the insertion aid may be configured to facilitate a handling of the medical device by the user and/or to reduce application errors. The insertion aid may at least partially surround the housing. Further, the insertion aid may be at least partially coupled to the housing.

The insertion aid may comprise a detachable lower cover mechanically coupled to the detachable lower cap. As further used herein, the term "cover" may refer to an arbitrary element that completely or at least to a large extend closes an object. Specifically, the cover may be or may comprise a shell, particularly a half-shell, surrounding the medical device. The detachable lower cover may be configured such that a removal of the detachable lower cover removes the detachable lower cap. The insertion aid may further comprise at least one upper cover. The upper cover may be directly or indirectly coupled to one or both of the insertion cannula or the detachable upper cap, such that a movement of the upper cover against the frame drives the insertion cannula. The terms "lower cover" and "upper cover" may be considered as description without specifying an order and without excluding a possibility that several kinds of lower covers and upper covers may be applied. The insertion aid may further comprise at least one frame. The term "frame" may refer to an arbitrary element which may be configured to support other components of a physical construction. The frame may be displaceable on the skin of the user and which at least partially surrounds the housing and the upper cover movable against the frame.

In a further aspect of the present invention, a method for assembling a medical device according to any embodiment as described above or as further described below is disclosed. The methods comprise the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for assembling the medical device comprises:
 a) providing at least one part of the housing, the at least one part of the housing comprising at least a part of the electronics compartment and the sensor compartment with the detachable upper cap and the detachable lower cap;
 b) placing the analyte sensor at least partially into the sensor compartment, wherein the analyte sensor and the at least one part of the housing provided in step a) form an intermediate product;
 c) sterilizing the intermediate product; and
 d) placing at least one electronics unit into the at least one part of the electronics compartment provided in step a).

The housing may be manufactured by injection molding. During step b) at least one further element may be placed at least partially into the sensor compartment. The at least one further element may be selected from the group consisted of: an insertion cannula, a sealing element, particularly a septum. The method may further comprise operably connecting, specifically electronically connecting, the analyte sensor with the electronics unit. The method may further comprise attaching at least one further part of the electronics compartment to the at least one part of the electronics compartment receiving the electronics unit, thereby forming the electronics compartment with the electronics unit received therein. Specifically, after conducting step d) the electronics compartment may be sealed by at least one cover.

Step c) may be conducted by at least one sterilization process based on radiation, particularly e-beam sterilization. The method may further comprise at least one step of sterilizing the electronics unit, particularly by gas sterilization.

Specifically, the method may be performed such that step c) is performed before performing step d), in order to avoid exposing the electronics unit to the radiation. Similarly, the sterilization of the electronics unit may be performed after placing the electronics unit into the electronics compartment or into the at least one part thereof, in a state in which the sensor compartment is sealed, such as by the detachable upper cap and the detachable lower cap. Consequently, for sterilizing the electronics unit, a gas sterilization may be used, such as by using ethylene oxide. Since the sensor compartment is sealed by the upper cap and the lower cap, the gas used for gas sterilizing the electronics unit may be prevented from entering the sensor compartment and, thus, may be prevented from affecting the analyte sensor or at least the insertable portion of the analyte sensor disposed therein.

By using this two-step sterilization, the specific requirements and sensitivities of the different components may be accounted for. Thus, generally, the electronics unit is sensitive against and may be damaged by high energy radiation, such as gamma rays or electron beams. Consequently, the radiation sterilization may be performed on the intermediate product, without the electronics unit being connected to the analyte sensor, in order to sterilize the analyte sensor or at least the insertable portion of the analyte sensor. Contrarily, the analyte sensor or typical sensor chemicals used therein in most cases are sensitive against and may be damaged by sterilizing gases such as ethylene oxide. Consequently, the sterilization of the electronics unit connected to the analyte sensor may be performed such that the sterilizing gas such as the ethylene oxide is prevented from interacting with the insertable portion of the analyte sensor. Consequently, the sterilization processes may be optimized independently, without taking the risk of destroying the electronics unit by radiation and without taking the risk of destroying the analyte sensor by sterilizing gas.

In a further aspect of the present invention, a method of using the medical device according to any embodiment as described above or as further described below is disclosed. The methods comprise the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method of using a medical device comprises:
I. providing the medical device;
II. removing the detachable lower cap;
III. inserting the analyte sensor into the body tissue; and
IV. removing the detachable upper cap, thereby removing the insertion cannula from the medical device.

The medical device may further comprise the at least one insertion aid comprising the at least one upper cover and the detachable lower cover as described above. Thereby, the method of using a medical device may further comprise:
i. removing detachable lower cover, thereby removing the detachable lower cap;
ii. inserting the analyte sensor into the body by applying an insertion mechanism via the upper cover.

The housing may comprise the at least one adhesive surface covered by at least one protective foil, wherein during step i. the protective foil is removed. Specifically, the detachable lower cover may be removed by a rotatory motion. However, other embodiments are feasible. The upper cover may comprise at least one spring drive and before conducting step i. the spring drive may be tightened thereby securing parts of the insertion mechanism, wherein after conducting step II., the insertion cannula is retracted by at least one spring.

The proposed medical package, the method for assembling a medical device and the method of using a medical device provide many advantages over known devices and methods.

Usually, common medical devices may initially comprise two components. The two components may form a final product after application of the medical device to the body tissue of the user. The analyte sensor may commonly have to be connected to the electronics unit via the user. This may specifically lead to errors during application and thus to severe consequences such as measurement errors. Therefore, in common medical devices, elaborate constructions may generally have to be realized to circumvent error sources. The elaborate constructions may exemplarily comprise sealings, electrical contacts or locking forces.

Specifically in case of analyte sensors which are electrochemical sensors, electronic components may generally not be treatable via beam sterilization. However, electrochemical sensors itself generally may only be treatable via beam sterilization so that a functionality of the electrochemical sensor may be ensured.

Therefore, the medical device according to the present invention may comprise a combination of a sterile compartment including the analyte sensor and the electronics unit which may specifically be a single-use electronics unit. The sterile compartment may be integrated into the electronics unit.

The user may receive an "all-in-one" medical device without a need for assembling the medical device. The medical device may further be robust and low-priced. An application of the medical device to the body tissue of the user may be conductible in a simple and intuitive manner.

Parts of the medical device may remain at the body tissue of the user after using the medical device. These parts may stay at the body tissue during a predetermined application period. A sterilization of the analyte sensor and a subsequent assembling of the electronics unit during assembling the medical device may be realized without opening the sealed compartment. Further, a compact and small construction as well as a simple assembling may be possible.

The housing, specifically the lower housing portion, may be manufactured by injection molding. Further, the housing may comprise the at least two predetermined breaking points. For assembling the medical device, the insertion cannula, the septum and/or the analyte sensor may be inserted into the housing. Thereafter, the opening connecting the electronics compartment and the sensor compartment to each other may be sealed. The handles may be attached to the detachable upper cap and to the detachable lower cap, respectively. The handles may optionally comprise the at least one desiccant or activated carbon. This assembly may be sterilized. The interconnect device may be placed on the lower housing portion and may be fixed to the lower housing portion, exemplarily via warm caulking. The analyte sensor may be operably connected to the interconnect device, specifically by a conductive adhesive material. The upper housing portion and the adhesive surface may be mounted. The adhesive surface may be mounted on the lower housing portion. The upper housing portion may be mounted tightly on the lower housing portion, exemplarily via laser welding or adhesive bonding. The medical device may be primary. and be optionally be secondary-packaged, wherein no great demands are placed on the packaging.

During using the medical device, the packaging may be opened by the user. The protective foil of the adhesive element may be removed and the detachable lower cap may be detached. The medical device may be mounted on the body tissue of the user and the analyte sensor may be inserted into the body tissue. The insertion cannula may be removed from the body tissue. Thereafter, the detachable upper cap may be detached from the medical device.

The septum may be an individual component or may be manufactured by injection molding. The barbed hook may be configured to prevent a second usage of the insertion cannula. The barbed hook may be an additional component or may be integrated as one component. The insertion cannula may be a tube or a stamped-bent part. The insertion cannula may be sealed by the septum. Therefore, the insertion cannula may specifically have a round cross-section. However, other embodiments such as a flat design are feasible.

The electronics compartment may be closed compartment or may be a potted mass. Specifically, the electronics compartment may be potted with an elastomeric material. Thereby, a flexible system may be attached to the body tissue of the user. This may lead to an increased wearing comfort. The electronics unit may specifically comprise a flexible printed circuit. Optionally, the lower housing portion may comprise stiff structures for mounting the adhesive surface.

The insertion aid may comprise the upper cover. The upper cover may be part of the primary packaging. Further, the user may use the upper cover for using the medical device. The upper cover may be fixedly connected to the detachable upper cap. The insertion aid may have the retraction mechanism configured to retract the insertion cannula automatically after the insertion cannula has been inserted into the body tissue. The detachable lower cover of the insertion aid may be part of the primary packaging. Further, the detachable lower cover may be fixedly connected to the detachable lower cap. During opening of the detachable lower cover the detachable lower cap may be opened at the same time and the adhesive surface may be exposed. The frame may protect the insertion cannula, specifically before using the medical device. The user may hold the medical device onto the body tissue. The frame may require an initial force such that the user may build up a force during manually inserting the insertion cannula and may insert quickly. The frame may trigger a mechanism such that the insertion cannula may be withdrawn automatically as soon as the frame is compressed. Specifically, the mechanism may be a spring-pretensioned mechanism. The insertion aid may provide an easy handling for the user.

The detachable lower cover may comprise a basis which is fixedly connected to a lower part of the detachable lower cap, exemplarily via a snap connection, an adhesive bonding and/or a longitudinal guide or transferring force. The basis may comprise gripping surfaces for detaching the detachable lower cover. The basis may at the same time be a cover for the adhesive surface. This may lead to an extended shelf-life of the adhesive surface. By detaching of the detachable lower cover the detachable lower cap may be opened, the insertion cannula and the analyte sensor may be exposed and the adhesive surface may be exposed at the same time.

The upper cover of the insertion aid may comprise the spring drive. The spring drive may be configured to trigger the insertion of the insertion cannula. The spring drive may be tensioned during pressing the electronics unit into the insertion aid. The insertion cannula may click into an element which may trigger a withdrawing of the insertion cannula after insertion.

The upper cover may comprise guiding elements such that a circulation of the electronics unit within the insertion aid is at least to a large extent suppressed. Exemplarily, the electronics unit may have a non-round shape, there may be guiding rails in an external shape of the electronics unit and/or there may be special structures such as nuts within the electronics unit.

The insertion aid may be triggered via a release button. The medical device may be shot on the body tissue. At a bottom dead center the spring drive may be released for withdrawing the insertion cannula. The insertion aid may be removed from the body tissue. The user may optionally detach the detachable upper cap with the insertion cannula by hand. Optionally, the user may tilt the insertion aid thereby detaching the detachable upper cap.

A tensioning of the medical device may be realized via a rotational movement. Thereby, the housing may be turned on and may be hold up from below. This may exemplarily be realized by a suitable formed primary packaging. Thereby, the primary packaging may be coupled with the detachable lower cap. Exemplarily, the insertion aid may be configured to conduct the rotational movement for detaching the detachable lower cap by itself. This may be realized as follows: During tensioning of the medical device two mechanisms may be tensioned. A first mechanism may refer to a spring system for inserting the analyte sensor into the body tissue as described above. A second mechanism may refer to the rotational movement as described above. The electronics unit may be fixed at a top dead center within the insertion aid. As soon as the electronics unit may be fixed there may be a rotational movement in a counter direction.

Alternatively, other mechanisms may be applied to remove the detachable upper cap from the electronics compartment such as a coupled mechanism which may be withdrawable in an easy manner, cutting a breaking point with a knife or turning off the detachable upper cap. The detachable upper cap does not need to be fixedly connected to the electronics compartment. To facilitate assembling of the medical device and/or to facilitate a removing the detachable upper cap by the user, the couple mechanism may be applied. Exemplarily, a tube-in-tube-system may be applied comprising a sealing with an elastic mass such as rubber, thermoplastic polymers or silicone.

Summarizing, the following embodiments are potential embodiments of the present invention. Other embodiments, however, are feasible.

Embodiment 1: A medical device for detecting at least one analyte in a body fluid, the medical device comprising:
  at least one analyte sensor having an insertable portion adapted for at least partially being inserted into a body tissue of a user, at least one insertion cannula, wherein the analyte sensor at least partially is placed inside the insertion cannula;

at least one electronics unit, wherein the analyte sensor is operably connected to the electronics unit;

at least one housing, wherein the housing comprises at least one electronics compartment configured to at least partially receive the electronics unit and at least one sensor compartment configured to at least partially receive the analyte sensor, wherein the sensor compartment forms a sealed compartment receiving at least the insertable portion of the analyte sensor, wherein the sealed compartment comprises at least one detachable upper cap and at least one detachable lower cap, wherein the detachable lower cap is configured for detachment before insertion, thereby opening the insertable portion for insertion, wherein the insertion cannula is attached to the detachable upper cap, wherein the detachable upper cap is configured for detachment after insertion, thereby removing the insertion cannula, wherein the electronics compartment at least partially surrounds the sensor compartment.

Embodiment 2: The medical device according to the preceding embodiment, wherein the electronics compartment and the sensor compartment are designed integrally.

Embodiment 3: The medical device according to the preceding embodiment, wherein the electronics compartment and the sensor compartment form a single piece.

Embodiment 4: The medical device according to any one of the preceding embodiments, wherein the electronics compartment and the sensor compartment share a common wall of the housing.

Embodiment 5: The medical device according to the preceding embodiment, wherein the common wall is at least partially designed as a cylindrical ring surrounding the insertion cannula.

Embodiment 6: The medical device according to any one of the preceding embodiments, wherein the sensor compartment comprises at least one intermediate component, wherein the detachable upper cap and the detachable lower cap are detachably connected to the intermediate component.

Embodiment 7: The medical device according to the preceding embodiment, wherein the detachable upper cap and the detachable lower cap are detachably connected to the intermediate component on opposing sides of the intermediate component.

Embodiment 8: The medical device according to any one of the two preceding embodiments, wherein the intermediate component at least partially is designed as a cylindrical ring surrounding the insertion cannula.

Embodiment 9: The medical device according to any one of the preceding embodiments, wherein the detachable upper cap is detachably connected to the intermediate component at at least one upper predetermined breaking point and wherein the detachable lower cap is detachably connected to the intermediate component at at least one lower predetermined breaking point.

Embodiment 10: The medical device according to the preceding embodiment, wherein the upper predetermined breaking point and the lower predetermined breaking point are ring-shaped breaking points.

Embodiment 11: The medical device according to any one of the five preceding embodiments, wherein the electronics compartment is connected to the intermediate component.

Embodiment 12: The medical device according to the preceding embodiment, wherein the electronics compartment at least partially surrounds the intermediate component.

Embodiment 13: The medical device according to any one of the two preceding embodiments, wherein the electronics compartment and the intermediate component share at least one common wall.

Embodiment 14: The medical device according to the preceding embodiment, wherein the intermediate component forms a wall of the electronics compartment.

Embodiment 15: The medical device according to any one of the preceding embodiments, wherein the medical device comprises at least one adhesive surface for attachment to a user's skin.

Embodiment 16: The medical device according to the preceding embodiment, wherein the adhesive surface is directly or indirectly attached to the housing.

Embodiment 17: The medical device according to any one of the two preceding embodiments, wherein the adhesive surface is a lower surface of the electronics compartment.

Embodiment 18: The medical device according to the preceding embodiment, wherein the insertable portion of the analyte sensor and the detachable lower cap extend from the lower surface of the electronics compartment.

Embodiment 19: The medical device according to any one of the four preceding embodiments, wherein the adhesive surface has a shape of a circular ring surrounding the analyte sensor.

Embodiment 20: The medical device according to any one of the five preceding embodiments, wherein the adhesive surface comprises at least one of plaster or an adhesive strip.

Embodiment 21: The medical device according to any one of the preceding embodiments, wherein the medical device is a disposable medical device.

Embodiment 22: The medical device according to any one of the preceding embodiments, wherein the electronics unit is a single-use electronics unit.

Embodiment 23: The medical device according to any one of the preceding embodiments, wherein the sensor compartment is configured to provide a sterile packaging for the insertable portion of the analyte sensor.

Embodiment 24: The medical device according to any one of the preceding embodiments, wherein the detachable lower cap is a sterile cap configured to provide sterile packaging for the insertable portion of the analyte sensor, such that the insertable portion is sealed against a surrounding environment.

Embodiment 25: The medical device according to any one of the preceding embodiments, wherein the detachable upper cap partially surrounds the insertion cannula.

Embodiment 26: The medical device according to any one of the preceding embodiments, wherein the insertion cannula is fixedly attached to the detachable upper cap.

Embodiment 27: The medical device according to any one of the preceding embodiments, wherein the detachable upper cap and/or the detachable lower cap comprise at least one predetermined breaking point configured for enabling a detaching of the detachable upper cap and/or the detachable lower cap by mechanical force.

Embodiment 28: The medical device according to any one of the preceding embodiments, wherein the electronics compartment and the sensor compartment are connected to each other via at least one sealed opening, wherein the analyte sensor passes through the sealed opening.

Embodiment 29: The medical device according to the preceding embodiment, wherein the analyte sensor is partially received in the electronics compartment and partially received in the sensor compartment, wherein the insertable portion at least partially is received in the sensor compartment.

Embodiment 30: The medical device according to any one of the two preceding embodiments, wherein the sealed opening comprises at least one sealing element, wherein the sealing element seals the sensor compartment from the electronics compartment.

Embodiment 31: The medical device according to the preceding embodiment, wherein the sealing element comprises at least one sealing lip.

Embodiment 32: The medical device according to any one of the two preceding embodiments, wherein the sealing element comprises at least one sealing material, particularly a deformable sealing material, more preferably an adhesive material.

Embodiment 33: The medical device according to any one of the preceding embodiments, wherein the insertion cannula comprises at least one barbed hook configured to prevent a further movement of the insertion cannula after usage.

Embodiment 34: The medical device according to any one of the preceding embodiments, wherein medical device further comprises at least one septum received in the sensor compartment, wherein the insertion cannula passes through the septum.

Embodiment 35: The medical device according to the preceding embodiment, wherein the insertion cannula is configured for being pulled through the septum when the detachable upper cap is detached from the housing.

Embodiment 36: The medical device according to any one of the two preceding embodiments, wherein the septum is configured for sealing a remainder of the sensor compartment after detachment of the detachable upper cap.

Embodiment 37: The medical device according to any one of the three preceding embodiments, wherein the septum is manufactured by injection molding, particularly by two-component injection molding.

Embodiment 38: The medical device according to any one of the preceding embodiments, wherein the detachable upper cap and/or the detachable lower cap comprise at least one handle.

Embodiment 39: The medical device according to the preceding embodiment, wherein the handle comprises at least one hygroscopic material, preferably at least one desiccant, more preferably activated carbon.

Embodiment 40: The medical device according to any one of the preceding embodiments, wherein the electronics compartment and the sensor compartment are at least partially formed by one single housing element.

Embodiment 41: The medical device according to any one of the preceding embodiments, wherein the housing is manufactured by injection molding.

Embodiment 42: The medical device according to any one of the preceding embodiments, wherein the electronics unit comprises at least one interconnect device, preferably a printed circuit board, more preferably a flexible printed circuit board.

Embodiment 43: The medical device according to the preceding embodiment, wherein the analyte sensor is electrically connected to the interconnect device, preferably via at least one of a conductive adhesive material or a plug connection.

Embodiment 44: The medical device according to any one of the two preceding embodiments, wherein the interconnect device is fixedly positioned within the electronics compartment of the housing.

Embodiment 45: The medical device according to any one of the preceding embodiments, wherein the electronics compartment comprises at least two housing portions.

Embodiment 46: The medical device according to the preceding embodiment, wherein the at least two housing portions comprise at least one lower housing portion and at least one upper housing portion.

Embodiment 47: The medical device according to any the preceding embodiment, wherein the lower housing portion comprises at least one lower surface configured for being placed on a user's skin.

Embodiment 48: The medical device according to any one of the two preceding embodiments, wherein the upper housing portion comprises one or more of a cover or an adhesive sealing material, more preferably at least one elastic material, particularly an elastic polymeric material.

Embodiment 49: The medical device according to any one of the three preceding embodiments, wherein the upper housing portion and the lower housing portion may be connected via one or more of a form-fit connection, a force-fit connection or a connection by material engagement, more specifically by a connection using at least one adhesive and/or at least one bonding.

Embodiment 50: The medical device according to any one of the four preceding embodiments, wherein the upper housing portion forms an encapsulation for electronics components of the electronics unit.

Embodiment 51: The medical device according to any one of the preceding embodiments, wherein the medical device further comprises at least one retraction mechanism for retracting the insertion cannula after insertion of the insertable portion of the analyte sensor into the body tissue.

Embodiment 52: The medical device according to the preceding embodiment, wherein the retraction mechanism is at least partially comprised within the detachable upper cap.

Embodiment 53: The medical device according to any one of the two preceding embodiments, wherein the retraction mechanism comprises at least one retraction spring element, more preferably at least one retraction spring element disposed in between the housing and the insertion cannula and biased in order to retract the insertion cannula from the body tissue.

Embodiment 54: The medical device according to any one of the preceding embodiments, wherein the medical device further comprises at least one insertion aid configured for enabling a user to drive the insertion cannula into the body tissue and to insert the insertable portion of the analyte sensor.

Embodiment 55: The medical device according to the preceding embodiment, wherein the insertion aid at least partially surrounds the housing.

Embodiment 56: The medical device according to any one of the two preceding embodiments, wherein the insertion aid at least partially is coupled to the housing.

Embodiment 57: The medical device according to any one of the three preceding embodiments, wherein the insertion aid comprises a detachable lower cover mechanically coupled to the detachable lower cap, wherein the detachable lower cover is configured such that a removal of the detachable lower cover removes the detachable lower cap.

Embodiment 58: The medical device according to any one of the four preceding embodiments, wherein the insertion aid comprises at least one frame displaceable on the skin of the user and which at least partially surrounds the housing and at least one upper cover movable against the frame, wherein the upper cover is directly or indirectly coupled to one or both of the insertion cannula or the detachable upper cap, such that a movement of the upper cover against the frame drives the insertion cannula.

Embodiment 59: Method for assembling a medical device according to any one of the preceding embodiments, wherein the method comprises:
a) providing at least one part of the housing, the at least one part of the housing comprising at least a part of the electronics compartment and the sensor compartment with the detachable upper cap and the detachable lower cap;
b) placing the analyte sensor at least partially into the sensor compartment, wherein the analyte sensor and the at least one part of the housing provided in step a) form an intermediate product;
c) sterilizing the intermediate product; and
d) placing at least one electronics unit into the at least one part of the electronics compartment provided in step a).

Embodiment 60: The method according to the preceding embodiment, wherein the method further comprises operably connecting, specifically electronically connecting, the analyte sensor with the electronics unit.

Embodiment 61: The method according to any one of the two preceding embodiments, wherein the method further comprises attaching at least one further part of the electronics compartment to the at least one part of the electronics compartment receiving the electronics unit, thereby forming the electronics compartment with the electronics unit received therein.

Embodiment 62: The method according to any one of the three preceding embodiments, wherein the housing is manufactured by injection molding.

Embodiment 63: The method according to any one of the preceding embodiments referring to a method for assembling a medical device, wherein during step b) at least one further element is placed at least partially into the sensor compartment, the at least one further element comprises at least one element selected from the group consisted of: an insertion cannula; a sealing element, particularly a septum.

Embodiment 64: The method according to any one of the preceding embodiments referring to a method for assembling a medical device, wherein step c) is conducted by at least one sterilization process based on radiation, particularly e-beam sterilization.

Embodiment 65: The method according to any one of the preceding embodiments referring to a method for assembling a medical device, the method further comprising at least one step of sterilizing the electronics unit, particularly by gas sterilization.

Embodiment 66: The method according to any one of the preceding embodiments referring to a method for assembling a medical device, wherein after conducting step d) the electronics compartment is sealed by at least one cover.

Embodiment 67: Method of using the medical device according to any one of the preceding claims referring to a medical device the method comprising:
I. providing the medical device;
II. removing the detachable lower cap;
III. inserting the analyte sensor into the body tissue; and
IV. removing the detachable upper cap, thereby removing the insertion cannula from the medical device.

Embodiment 68: The method of using a medical device according to the preceding embodiment, wherein the medical device further comprises at least one insertion aid, wherein the insertion aid comprises at least one upper cover being attached to the detachable upper cap, wherein the insertion aid comprises at least one detachable lower cover being attached to the detachable lower cap, wherein the method of using a medical device further comprises:
i. removing the detachable lower cover, thereby removing the detachable lower cap;
ii. inserting the analyte sensor into the body by applying an insertion mechanism via the detachable upper cover.

Embodiment 69: The method of using a medical device according to the preceding embodiment, wherein the housing comprises at least one adhesive surface covered by at least one protective foil, wherein during step i. the protective foil is removed.

Embodiment 70: The method of using a medical device according to any one of the two preceding embodiments, wherein the detachable lower cover is removed by a rotatory motion.

Embodiment 71: The method of using a medical device according to any one of the three preceding embodiments, wherein the upper cover comprises at least one spring drive, wherein before conducting step i. the spring drive is tightened thereby securing parts of the insertion mechanism, wherein after conducting step ii. the insertion cannula is retracted by at least one spring.

SHORT DESCRIPTION OF THE FIGURES

Further details of the invention may be derived from the following disclosure of preferred embodiments. The features of the embodiments may be realized in an isolated way or in any combination. The invention is not restricted to the embodiments. The embodiments are schematically depicted in the figures. Identical reference numbers in the figures refer to identical elements or functionally identical elements or elements corresponding to each other with regard to their functions.

Figure 2:
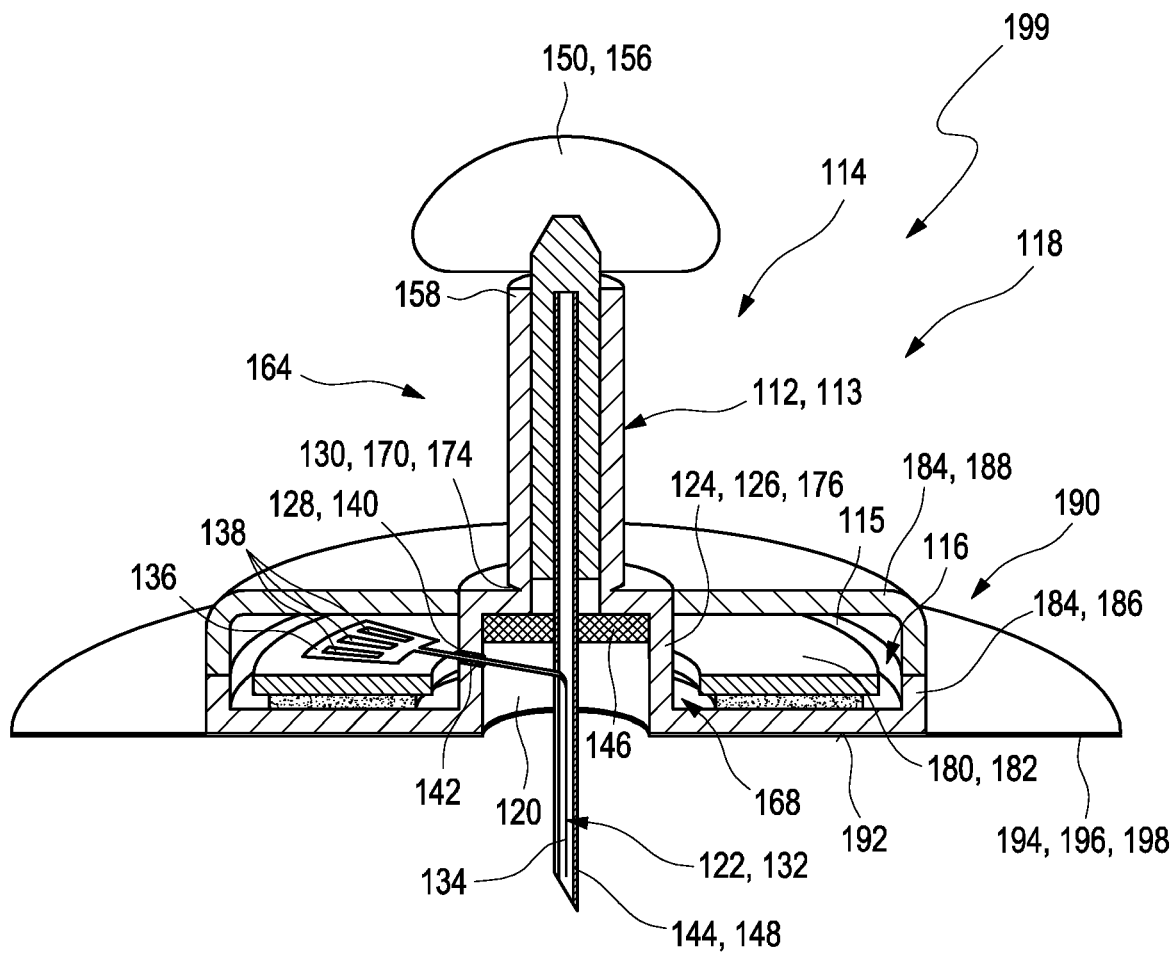
Figure 2:
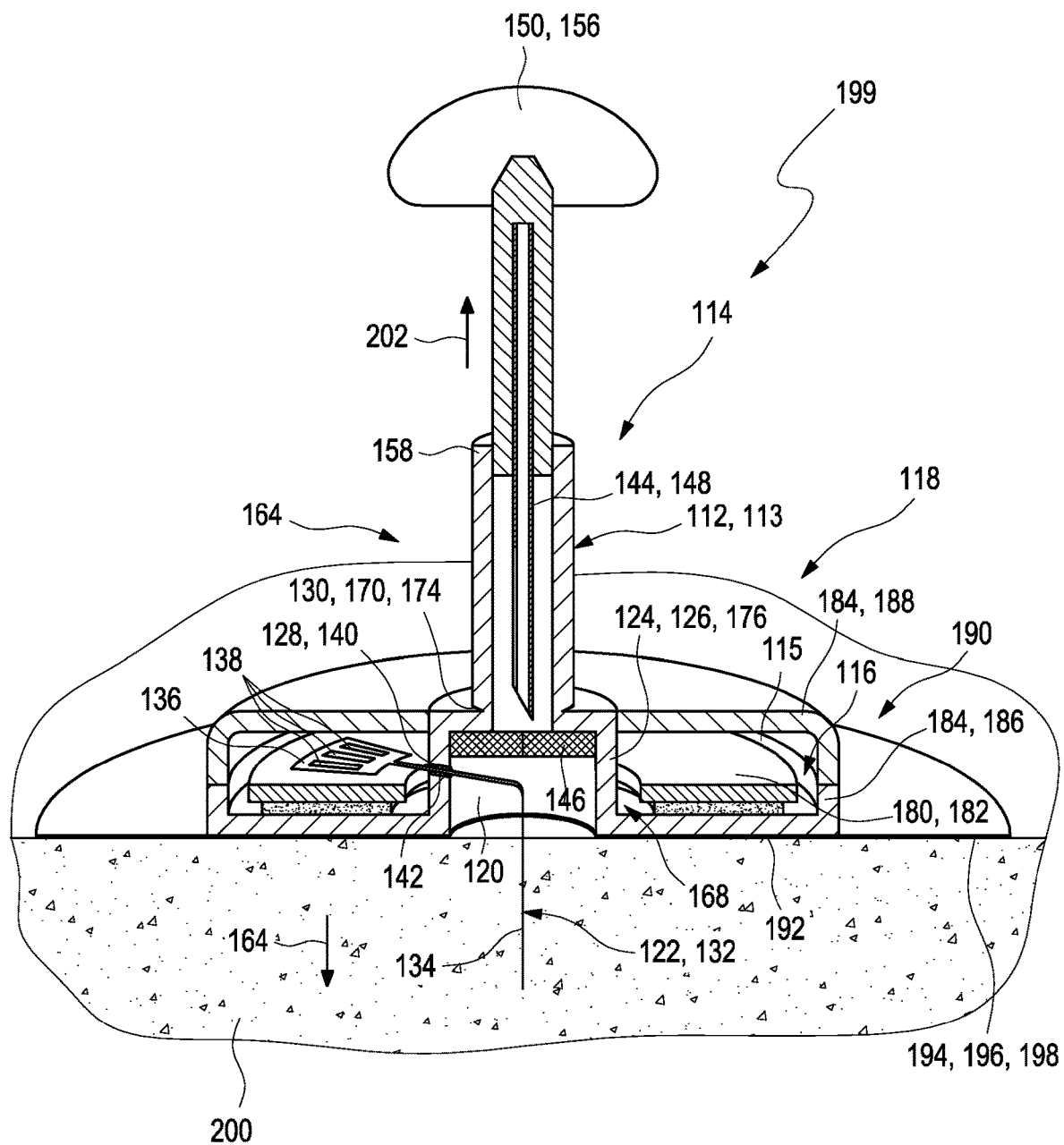
Figure 2:
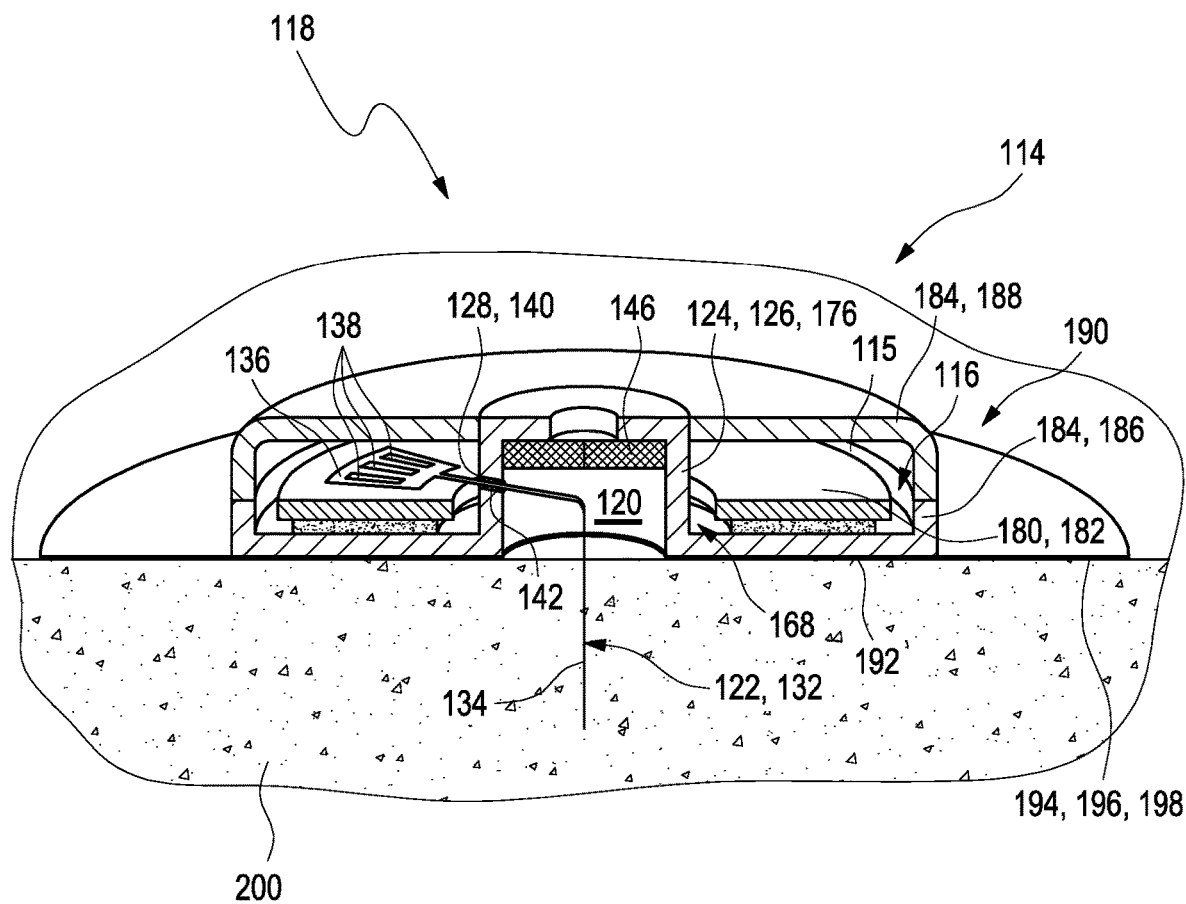
Figure 3:
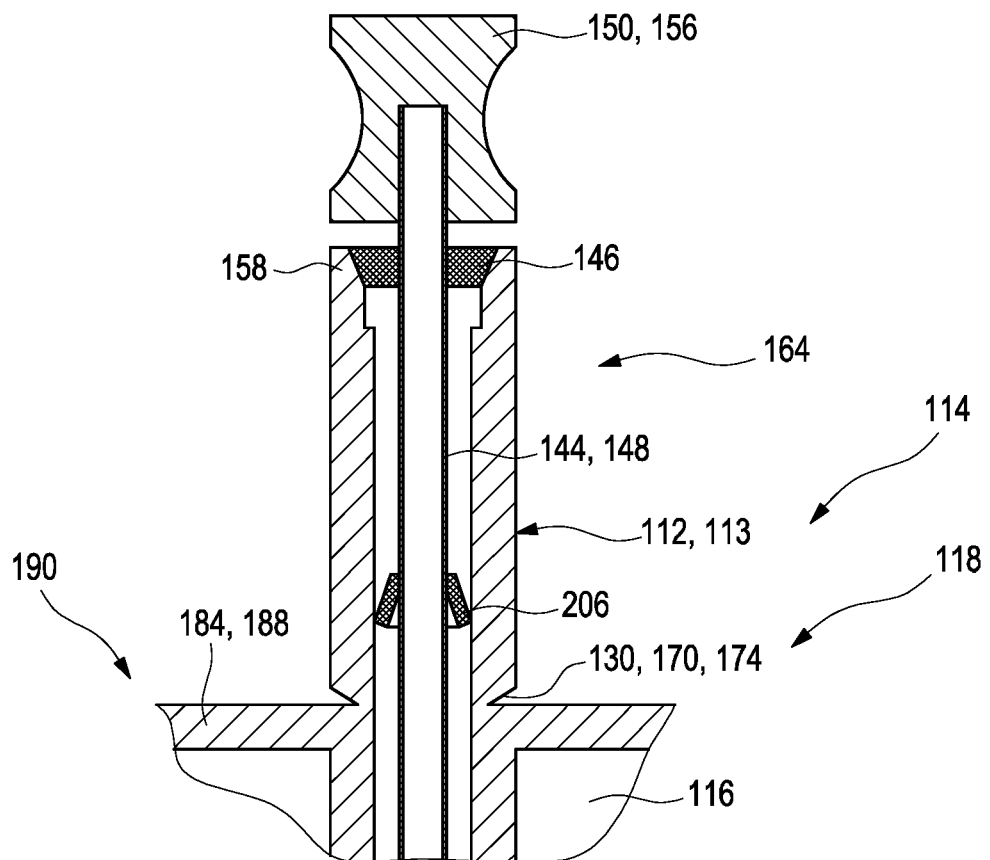
Figure 4:
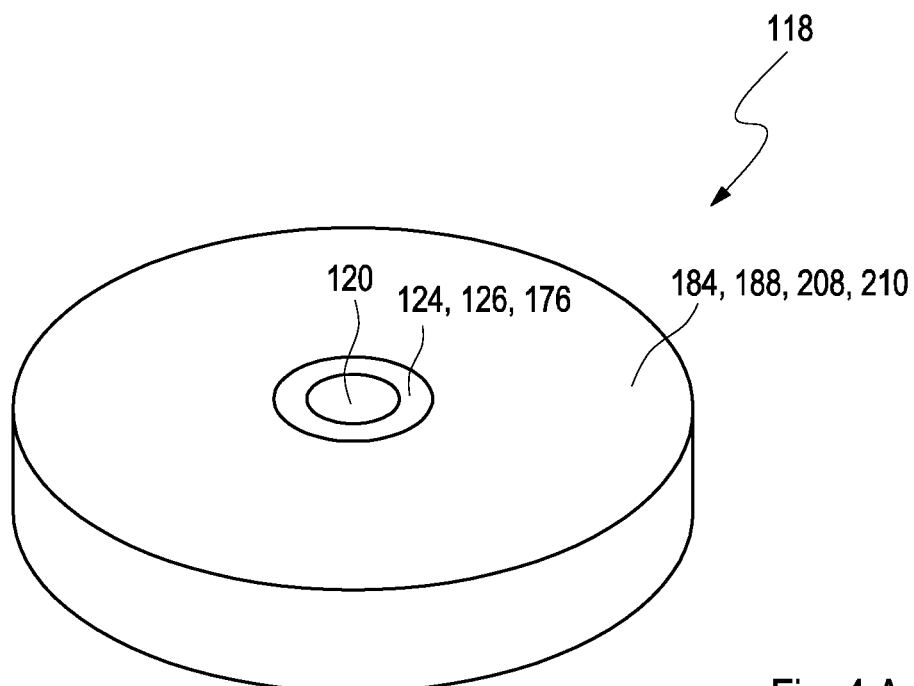
Figure 4:
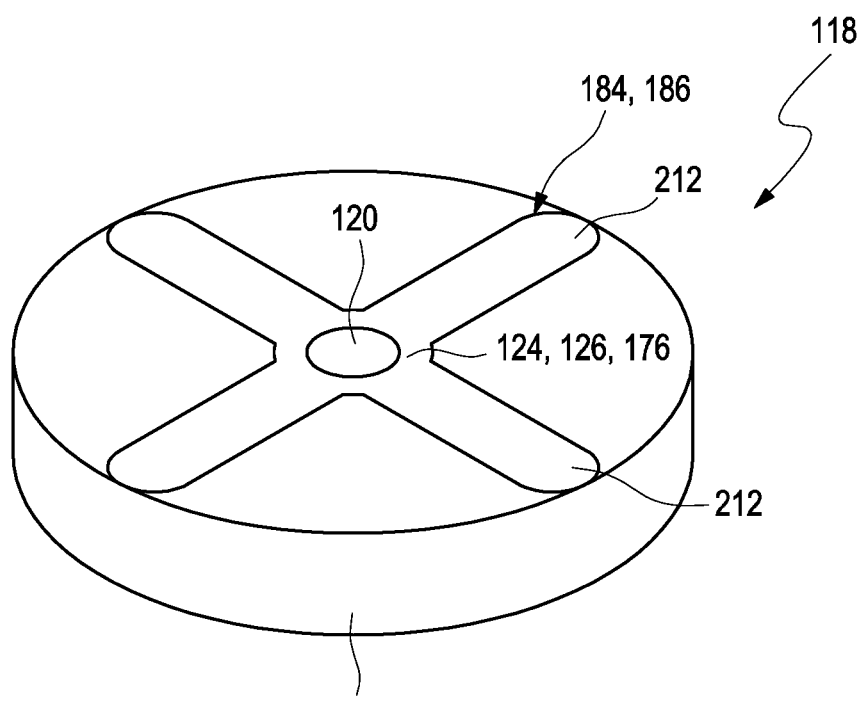
Figure 4:
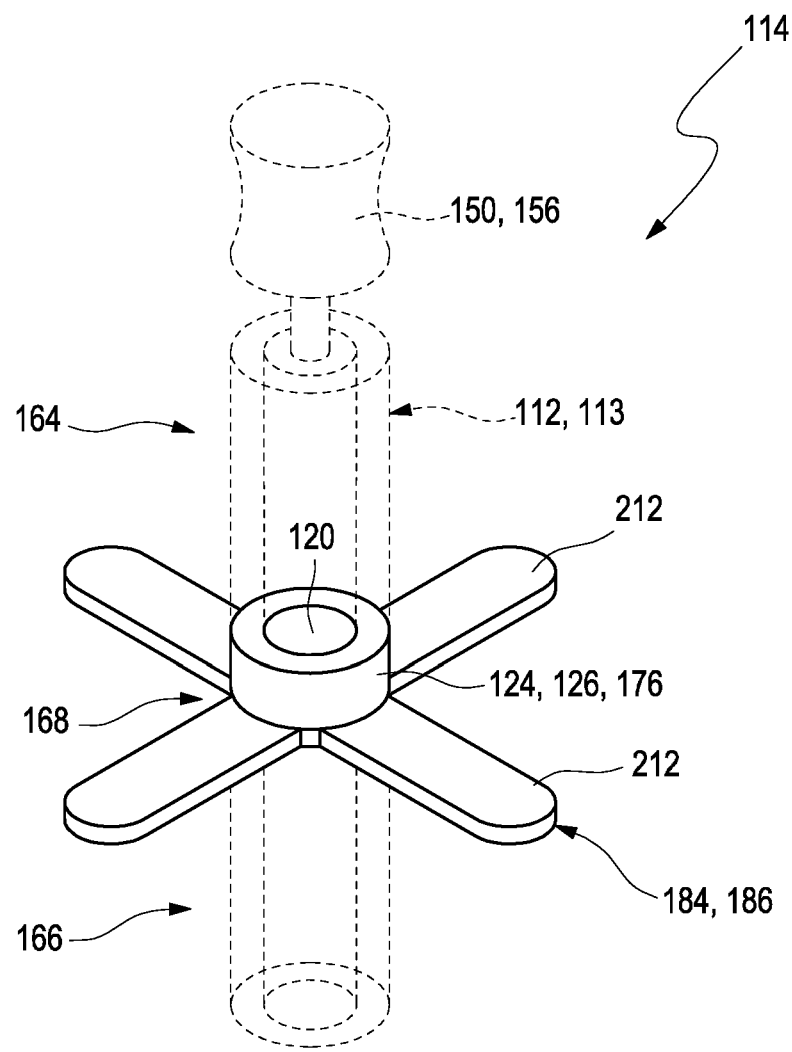
Figure 5:
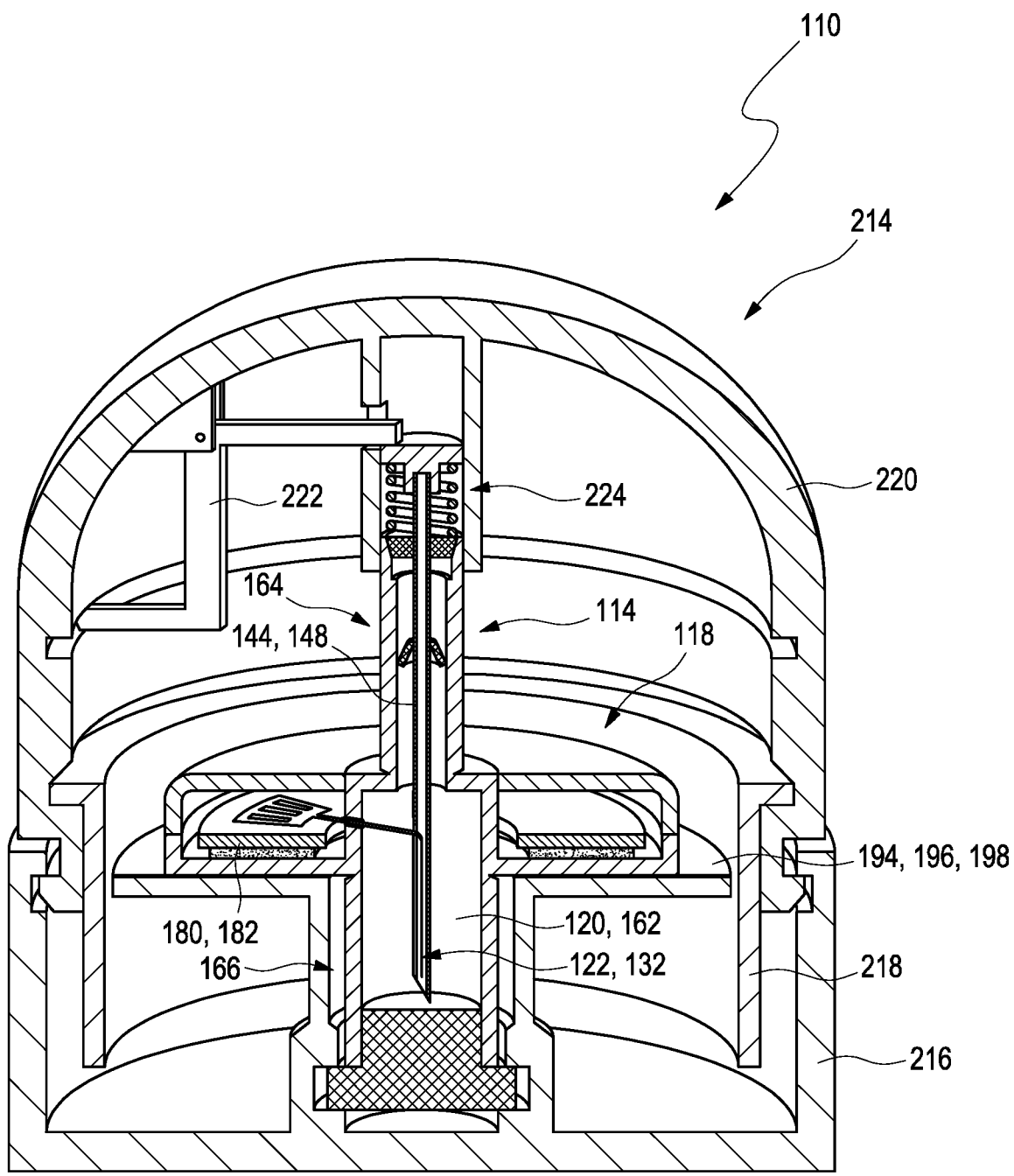
Figure 5:
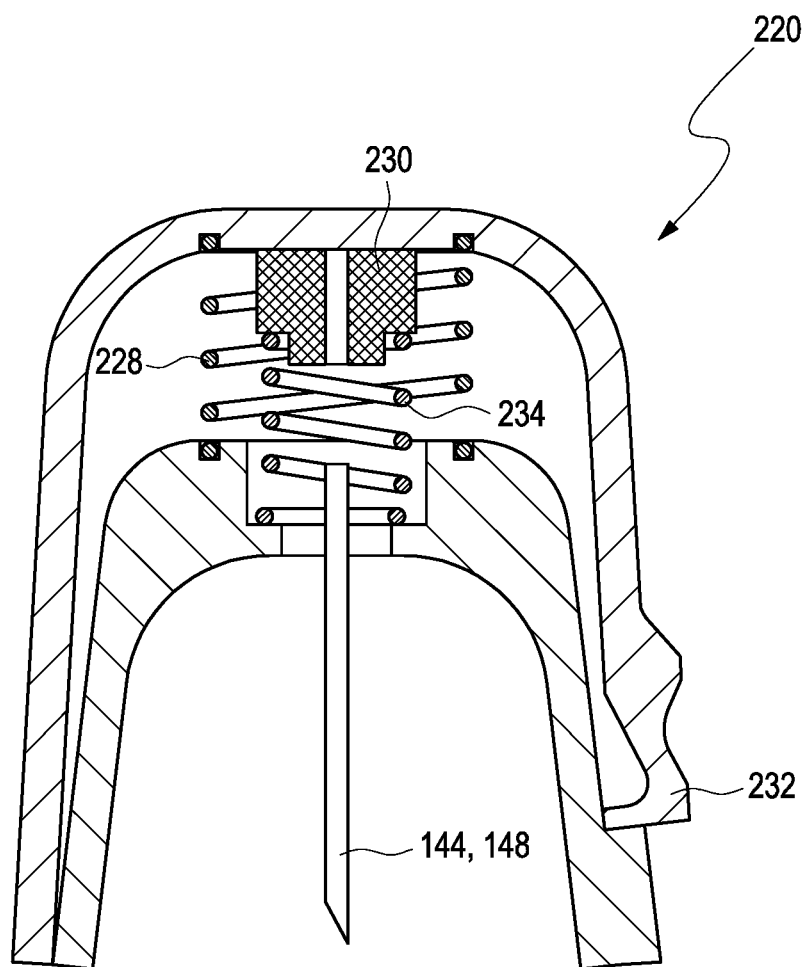

In the figures:
FIGS. 1A to 1D show an exemplary embodiment of a method for assembling a medical device;
FIGS. 2A to 2C show an exemplary embodiment of a method of using a medical device;
FIG. 3 shows an exemplary embodiment of a detachable upper cap in a cross-sectional view;
FIGS. 4A to 4C shows an exemplary embodiment of an electronics unit in different perspective views (FIGS. 4A and 4B) and a housing in a perspective view (FIG. 4C);
FIGS. 5A to 5B show an exemplary embodiment of a medical device (FIG. 5A) and an exemplary upper cover (FIG. 5B) in cross-sectional views; and
FIGS. 6A to 6B show an exemplary embodiment of a medical device in a cross-sectional view (FIG. 6A) and in a back view (FIG. 6B).

DETAILED DESCRIPTION OF THE EMBODIMENTS

In FIGS. 1A to 1D, an exemplary embodiment of a method for assembling a medical device 110 is shown. Thereby, FIGS. 1A to 1C show semi-manufactured products 111 of the medical device 110, whereas the medical device 110 is illustrated in FIG. 1D. However, other embodiments of the medical device 110 are feasible.

In a first step, as shown in FIG. 1A, at least one part 112 of a housing 114 is provided. The part 112 may specifically be a lower housing portion 113 of the housing 114. The housing 114 may specifically be manufactured by injection molding. The housing 114 may comprise at least one part 115 of an electronics compartment 116 configured to at least partially receive an electronics unit 118 as will further be described below. Further, the housing 114 comprises at least one sensor compartment 120 configured to at least partially receive an analyte sensor 122 as will further be described below.

The electronics compartment 116 and the sensor compartment 120 may be designed integrally. Thus, the electronics compartment 116 and the sensor compartment 120 may form a single piece. Specifically, the electronics compartment 116 and the sensor compartment 120 may share a common wall 124 of the housing 114. The common wall 124 may be at least partially designed as a cylindrical ring 126. The electronics compartment 116 and the sensor compartment 120 may be connected to each other via at least one opening 128. Further, the housing 114 may comprise predetermined breaking points 130 which will further be described below.

In a second step, as shown in FIG. 1B, the analyte sensor 122 is at least partially placed into the sensor compartment 120. The analyte sensor 122 may specifically be a transcutaneous sensor 132. The transcutaneous sensor 132 may be adapted to be fully or at least partially arranged within a body tissue of a patient or a user. For this purpose, the analyte sensor 122 comprises an insertable portion 134. The insertable portion 134 may be configured to be insertable into the body tissue. Beyond, the analyte sensor 122 may comprise at least one further portion 136 which may be configured to stay outside of the body tissue and may be connectable to the electronics unit 118. Thus, the further portion 136 may comprise one or more electrodes 138 configured for being connectable to the electronics unit 118. The analyte sensor 122 may pass through the opening 128. Specifically, the analyte sensor 122 is partially received in the electronics compartment 116 and partially received in the sensor compartment 120. The insertable portion 134 may at least partially be received in the sensor compartment 120. The opening 128 may be sealed and thus form a sealed opening 140. The sealed opening 140 may comprise at least one sealing element 142. The sealing element 142 may seal the sensor compartment 120 from the electronics compartment 116. The sealing element 142 may comprise at least one sealing material, particularly a deformable sealing material, more preferably an adhesive material.

Further, at least one insertion cannula 144 and at least one septum 146 may be placed at least partially into the sensor compartment 120. The analyte sensor 122 is at least partially placed inside the insertion cannula 144. Exemplarily, the insertion cannula 144 may be a hollow tube and may have a round cross section. Still, other embodiments are feasible. Specifically, the insertion cannula 144 may be a slotted cannula 148. The insertion cannula 144 may be configured to be inserted vertically to the body tissue of the user.

The septum 146 may be made of an elastic material such as an elastomer and may be manufactured by injection molding. The septum 146 may be penetrable by the insertion cannula 144. Further, the septum 146 may be configured for sealing the sensor compartment 120 from a surrounding environment. Further, at least two handles 150 may be mounted. A first handle 152 may be located on a lower end 154 of the sensor compartment 120, and a second handle 156 may be located at an upper end 158 of the sensor compartment 120. The first handle 152 and/or the second handle 156 may optionally comprise at least one hygroscopic material.

The sensor compartment 120 forms a sealed compartment 162. The sealed compartment 162 receives the insertable portion 134 of the analyte sensor 122. Further, the sealed compartment 162 comprises at least one detachable upper cap 164 and at least one detachable lower cap 166. The detachable lower cap 166 is configured for detachment before insertion, thereby opening the insertable portion 134 for insertion. The insertion cannula 144 is attached to the detachable upper cap 164, and the detachable upper cap 164 is configured for detachment after insertion, thereby removing the insertion cannula 144. Thus, the detachable upper cap 164 may partially surround the insertion cannula 144. The insertion cannula 144 may be fixedly attached to the detachable upper cap 164.

The sensor compartment 120 may comprise at least one intermediate component 168. The electronics compartment 116 may at least partially surround the intermediate component 168. Specifically, the electronics compartment 116 and the intermediate component 168 may share at least one common wall 176.

The detachable upper cap 164 and the detachable lower cap 166 may be detachably connected to the intermediate component 168. Specifically, the detachable upper cap 164 and the detachable lower cap 166 may be detachably connected to the intermediate component 168 on opposing sides of the intermediate component 168. The detachable upper cap 164 may be detachably connected to the intermediate component 168 at at least one upper predetermined breaking point 170, and the detachable lower cap 166 may be detachably connected to the intermediate component 168 at at least one lower predetermined breaking point 172. The upper predetermined breaking point 170 and/or the lower predetermined breaking point 172 may be ring-shaped breaking points 174.

The analyte sensor 122 and the at least one part 112 of the housing 114 form an intermediate product 178. The intermediate product 178 is sterilized. Specifically, at least one sterilization process based on radiation, particularly e-beam sterilization, may be applied. Thus, the detachable lower cap 166 may be a sterile cap 179 configured to provide a sterile packaging 181 for the insertable portion 134 of the analyte sensor 122.

In a further step, as illustrated in FIG. 1C, the at least one electronics unit 116 is placed into the at least one part 115 of the electronics compartment 116. The electronics unit 118 may comprise at least one interconnect device 180, preferably a printed circuit port 182. The analyte sensor 122 is operably connected to the electronics unit 118. Specifically, the analyte sensor 122 may be electrically connected to the interconnect device 180, preferably via at least one of a conductive adhesive material or a plug connection. The interconnect device 180 may be fixedly positioned within the electronics compartment 116 of the housing 114.

The electronics compartment 116 may comprise at least two housing portions 184. Specifically, the electronics compartment 116 may comprise at least one lower housing portion 186 and at least one upper housing portion 188. In a further step, as shown in FIG. 1D, the upper housing portion 188 may be mounted on the lower housing portion 186. The upper housing portion 188 may comprise a cover 190. The cover 190 may be connected to the lower housing portion 186 via one or more of a form-fit connection, a force-fit connection or a connection by material engagement, more specifically by a connection using at least one adhesive and/or at least one bonding.

The lower housing portion 186 may comprise at least one lower surface 192 configured for being placed on a user's skin. Therefore, at least one adhesive surface 194 may be mounted on the lower surface 192 of the lower housing portion 186. The adhesive surface 194 may be configured for attachment to the user's skin. Therefore, the adhesive surface 194 may comprise at least one of a plaster 196 or an adhesive strip 198. The adhesive surface 194 may have a shape of a circular ring surrounding the analyte sensor 122. The insertable portion 134 of the analyte sensor 122 and the detachable lower cap 166 may extend from the lower surface 192 of the electronics compartment 116.

FIGS. 2A to 2C show an exemplary embodiment of a method of using a medical device 110. In a first step, the medical device 110 as illustrated in FIG. 1D is provided. Thus, reference may be made to the description of FIG. 1D above. Within FIGS. 2A to 2C, diverse intermediate stages 199 of the medical device 110 are shown.

In a first step, as shown in FIG. 2A, the detachable lower cap 164 is removed. Thus, the insertion cannula 144 comprising the insertable portion 134 of the analyte sensor 122 may be exposed. Further, a protective foil covering the adhesive surface 194 which is not illustrated within FIG. 2A may be removed and the adhesive surface 194 may be uncovered.

In a further step, as illustrated within FIG. 2B, the analyte sensor 122 is inserted into a body tissue 200 of the user. Thereafter, the insertion cannula 144 may be withdrawn such that the insertion cannula 144 may be moved in a direction 202 opposing an insertion direction 160. Thereby, the insertion cannula 144 may be completely located within the detectable upper cap 164.

In a further step, as shown in FIG. 2C, the detachable upper cap 164 as illustrated within FIGS. 2A and 2B is removed, thereby removing the insertion cannula 144 from the medical device 110. The sensor compartment 120 may be sealed by the septum 146.

FIG. 3 shows an exemplary embodiment of a detachable upper cap 164 in a cross-sectional view. The detachable upper cap 164 corresponds at least in wide parts to the detachable upper cap 164 as illustrated within FIGS. 1A to 2C. Thus, reference may be made to the description of FIGS. 1A to 2C above.

The detachable upper cap 164 may comprise the septum 146. The septum 146 may be located at one end 204 of the detachable upper cap 164 opposing the electronics compartment 116. Further, the insertion cannula 144 may comprise at least one barbed hook 206. The barbed hook 206 may be configured to prevent a further movement of the insertion cannula 144 after usage. The barbed hook 206 may surround the insertion cannula 144 and may be located between the insertion cannula 144 and the detachable upper cap 164.

FIGS. 4A and 4B show an exemplary embodiment of an electronics unit 118 in different perspective views and FIG. 4C shows a corresponding housing 114 in a perspective view. The electronics unit 118 and the housing 114 resemble at least in large parts to the electronics unit 118 and the housing 114 as described within FIGS. 1A to 2C. Thus, reference may be made to the description of FIGS. 1A to 2C above.

The upper housing portion 188 of the housing 114 may form an encapsulation 208 for electronic components of the electronics unit 118. Therefore, the encapsulation 208 may be made of at least one elastomeric material. The encapsulation 208 may specifically be a potted mass 210. Consequently, a flexible system may be attachable to the body tissue 210 of the user. This may lead to an increased wearing comfort. The housing 114, specifically the lower housing portion 186 may provide at least one stiff area 212. The stiff area 212 may be configured for mounting the adhesive surface 194 as depicted in FIGS. 1A to 2C.

FIGS. 5A to 5B show an exemplary embodiment of a medical device 110 (FIG. 5A) and of an exemplary upper cover 220 (FIG. 5B) in cross-sectional views. The medical device 110 corresponds at least in large parts to the medical device 110 as described within FIGS. 1A to 2C. Thus, reference may be made to the description of FIGS. 1A to 2C above.

The medical device 110 further comprises at least one insertion aid 214 configured for enabling the user to drive the insertion cannula 144 into the body tissue 200 and to insert the insertable portion 134 of the analyte sensor 122. The insertion aid 214 may at least partially surround the housing 114. Further, the insertion aid 214 may be at least partially coupled to the housing 114. Specifically, the insertion aid 214 comprises a detachable lower cover 216 mechanically coupled to the detachable lower cap 166. The detachable lower cover 216 may be configured such that a removal of the detachable lower cover 216 removes the detachable lower cap 166.

Further, the insertion aid 214 may comprise at least one frame 218 displaceable on the skin of the user. The frame 218 may at least partially surround the housing 114. Further, the insertion aid 214 may comprise at least one upper cover 220. The upper cover 220 may be directly or indirectly coupled to one or both of the insertion cannula 144 or the detachable upper cap 164, such that a movement of the upper cover 220 against the frame 218 may drive the insertion cannula 144. Therefore, the upper cover 220 may be movable against the frame 218. The frame 218 may require an initial force such that the user may build up a force during manually inserting the insertion cannula 144 and may insert quickly. The frame 218 may be configured to trigger a retraction mechanism 222 such that the insertion cannula 144 may be withdrawn automatically as soon as the frame 218 is compressed. Specifically, the retraction mechanism 222 may comprise a spring-pretensioned mechanism 224. Further details may be described below within FIG. 5B.

The upper cover 220 of the insertion aid 214 as illustrated in FIG. 5B may comprise a spring drive 228. The spring drive 228 may be configured to trigger the insertion of the insertion cannula 144. The spring drive 228 may be tensioned during pressing of the electronics unit 118 into the insertion aid 214. The insertion cannula 144 may click into an element 230 which may be configured to trigger a withdrawing of the insertion cannula 144 after insertion. The insertion aid 214 may be triggered via a release button 232. Further, the insertion aid 214 may comprise at least one spring 234. Specifically, the insertion aid 214 may be configured such that the spring 234 may be released for withdrawing of the insertion cannula 144 at a bottom dead center.

FIGS. 6A and 6B show an exemplary embodiment of a medical device 110 in a cross-sectional view (FIG. 6A) and in a back view (FIG. 6B). The medical device 110 corresponds at least in large parts to the medical device 110 as described within FIGS. 1A to 2C. Thus, reference may be made to the description of FIGS. 1A to 2C above.

Further, an exemplary embodiment of an insertion aid 214 is shown. The insertion aid 214 may comprise the detachable lower cover 216. The detachable lower cover 216 may comprise a basis 236 which is connected to the detachable lower cap 166, exemplarily via a snap-connection 238. The basis 236 may comprise grips 240 for detaching the detachable lower cover 216, particularly via a rotational movement which is schematically illustrated with an arrow 242. The basis 236 may at the same time be a cover 244 for the adhesive surface 194. During detaching of the detachable lower cover 216 the detachable lower cap 166 may be opened, the insertion cannula 144 and the analyte sensor 122 may be exposed and the adhesive surface 192 may be exposed at the same time.

LIST OF REFERENCE NUMBERS 110 medical device
111 semi-manufactured product
112 part
113 lower housing portion
114 housing
115 part
116 electronics compartment
118 electronics unit
120 sensor compartment
122 analyte sensor
124 common wall
126 cylindrical ring
128 opening
130 predetermined breaking point
132 transcutaneous sensor
134 insertable portion
136 further portion
138 electrodes
140 sealed opening
142 sealing element
144 insertion cannula
146 septum
148 slotted cannula
150 handle
152 first handle
154 lower end
156 second handle
158 upper end
160 insertion direction
162 sealed compartment
164 detachable upper cap
166 detachable lower cap
168 intermediate component
170 upper predetermined breaking point
172 lower predetermined breaking point
174 ring-shaped breaking point
176 common wall
178 intermediate product
179 sterile cap
180 interconnect device
181 sterile packaging
182 printed circuit board
184 housing portion
186 lower housing portion
188 upper housing portion
190 cover
192 lower surface
194 adhesive surface
196 plaster
198 adhesive strip
199 intermediate stage
200 body tissue
202 direction
204 end
206 barbed hook
208 encapsulation
210 potted mass
212 stiff area
214 insertion aid
216 detachable loser cover
218 frame
220 upper cover
222 retraction mechanism
224 spring-pretensioned mechanism
226 spring drive
228 spring drive
230 element
232 release button
234 spring
236 basis
238 snap-connection
240 grip
242 arrow
244 cover

The invention claimed is:

1. An assembly of components for mounting an analyte sensor and an electronics compartment on a user, the assembly comprising:
a housing defining a sealed sensor compartment, the housing comprising an upper cap, a lower cap, and an electronics compartment, the electronics compartment receiving at least a portion of an electronics unit;
an analyte sensor comprising an insertable portion, the insertable portion being adapted for at least being partially inserted into a user's body tissue; and
a cannula attached to the upper cap, the insertable portion of the analyte sensor being received inside the cannula,
an insertion aid configured for driving the cannula into the user's skin, and for inserting the insertable portion of the analyte sensor into the user's skin,
the electronics compartment and the sealed sensor compartment being connected to each other via at least one sealed opening, the analyte sensor extending from the sealed sensor compartment through the sealed opening to the electronics compartment,
the analyte sensor being operably connected to the electronics unit,
the electronics compartment defining a cannula aperture extending from an upper surface opening to a lower surface opening,
the lower cap being configured to seal with the lower surface opening of the electronics compartment, the lower cap comprising an interior volume receiving the cannula and the insertable portion of the analyte sensor,
the upper cap being configured to seal with the upper surface opening of the electronics compartment,
the lower cap being configured for removal prior to insertion of the analyte sensor,
the upper cap and the cannula being configured for removal from the electronics compartment after insertion of the analyte sensor,
the cannula extending downwardly from the upper cap, through the cannula aperture, and beyond the lower surface opening, the insertable portion of the analyte sensor extending downwardly within the cannula and beyond the lower surface opening, and the lower cap extending downwardly from the electronics compartment,
the housing having a sealed condition, prior to insertion of the analyte sensor, in which the upper cap, the lower cap and the electronics compartment form the sealed sensor compartment surrounding and sealing the cannula and the insertable portion of the analyte sensor from an external environment, the upper cap and the electronics compartment being configured to move together to insert the cannula and the insertable portion of the analyte sensor into the user's body tissue, and the upper cap and the cannula being configured to be removed together from the user's body tissue after insertion of the insertable portion of the analyte sensor, leaving the analyte sensor implanted in the user's body tissue.

2. The assembly of claim 1 in which the cannula and analyte sensor are configured to move together from a non-insertion position outside the user's skin to an insertion position with the cannula extending into the user's skin.

3. The assembly of claim 1 in which the insertion aid comprises an insertion mechanism configured such that a user may apply to the cannula a force in a direction of insertion of the cannula.

4. The assembly of claim 1 in which the insertion aid is coupled to and at least partially surrounds the housing.

5. The assembly of claim 4 in which the electronics compartment is configured to move from a non-contact position away from the user's skin to a contact position on the user's skin simultaneous with the cannula, the analyte sensor and the upper cover moving from the non-insertion position to the insertion position.

6. The assembly of claim 1 in which the insertion aid includes an upper cover directly or indirectly coupled to one or both of the cannula or the upper cap.

7. The assembly of claim 6 in which the cannula, the analyte sensor, the upper cap, and the upper cover are configured to move together in the direction of insertion to insert the cannula and analyte sensor into the user's body tissue.

8. The assembly of claim 7 configured to build up an insertion force as the upper cover is pressed to insert the cannula.

9. The assembly of claim 7 in which the electronics compartment is configured to move from a non-contact position away from the user's skin to a contact position on the skin, simultaneous with the cannula, the analyte sensor, the upper cap and the upper cover being configured to move from the non-insertion position to the insertion position.

10. The assembly of claim 1 in which the insertion aid comprises a frame displaceable on the user's skin, and the cannula and the analyte sensor are configured to move together relative to the frame from the non-insertion position to the insertion position.

11. The assembly of claim 10 in which the frame is configured to protect the cannula prior to analyte sensor insertion.

12. The assembly of claim 11 in which the frame at least partially surrounds the housing.

13. The assembly of claim 12, wherein the frame is configured to trigger a retraction mechanism such that the insertion cannula is withdrawn from the skin automatically as soon as the frame is compressed.

14. The assembly of claim 13, wherein the retraction mechanism is a spring-pretensioned mechanism.

15. The assembly of claim 14 in which the insertion aid further includes an upper cover directly or indirectly coupled to one or both of the cannula and the upper cap, the cannula, the analyte sensor, the upper cap, and the upper cover being configured to move together relative to the frame from the non-insertion position to the insertion position.

16. The assembly of claim 1 in which the insertion aid comprises a frame configured to be displaced on the user's skin to support the analyte sensor and the electronics compartment during electronics compartment placement.

17. The assembly of claim 16 in which the electronics compartment is configured to move relative to the frame from the non-contact position to the contact position.

18. The assembly of claim 17 in which the assembly further comprises an upper cover.

19. The assembly of claim 18 in which, in the non-contact position, the electronics compartment is recessed inside the upper cover.

20. The assembly of claim 19 in which the upper cover and the electronics compartment are configured to move together from the non-contact position to the contact position.

21. The assembly of claim 20 in which the upper cover is configured to be pressed to move the electronics compartment from the non-contact position to the contact position to place the electronics compartment on the user's skin.

22. The assembly of claim 1 in which the insertion aid comprises a frame configured to be displaced on the user's skin during analyte sensor insertion to support the analyte sensor and the electronics compartment during electronics compartment placement.

23. The assembly of claim 22 in which the cannula and the analyte sensor are configured to move relative to the frame from the non-insertion position to the insertion position, and the electronics compartment is configured to move relative to the frame from the non-contact position to the contact position.

24. The assembly of claim 23 in which the cannula and analyte sensor are configured to move from the non-insertion position to the insertion position together with the electronics compartment moving from the non-contact position to the contact position.

25. The assembly of claim 24 in which the assembly further comprises an upper cover configured to simultaneously:

move with the cannula and analyte sensor to insert the cannula and the analyte sensor into the user's skin, and move with the electronics compartment from the non-contact position to the contact position to place the electronics compartment on the user's skin.

26. An analyte monitoring system comprising:

an assembly according to claim 1, the electronics unit comprising an electronic component configured for performing a measurement with the analyte sensor, a device for recording sensor signals, a device for storing measurement signals or measurement data, a transmitter for transmitting sensor signals and/or measurement data, and an energy source; and a second device, the transmitter transmitting the sensor signals and/or measurement data to the second device.

27. A method for mounting an analyte sensor and an electronics compartment on a user using an assembly according to claim 1, the assembly further comprising an insertion aid comprising a frame displaceable on the user's skin to support the analyte sensor and the electronics compartment during insertion of the cannula and the analyte sensor, the upper cap, the cannula and the electronics compartment being configured to move together in the direction of insertion to insert the cannula and the insertable portion of the analyte sensor into the user's body tissue, and to mount the electronics compartment on the user's skin, the method comprising:

removing the lower cap from the electronics compartment;

displacing the frame on the user's skin;

advancing the upper cap, the cannula and the electronics compartment in the direction of insertion to insert the cannula and the insertable portion of the analyte sensor into the user's body tissue, and to mount the electronics compartment on the user's skin, the upper cap, the cannula, and the electronics compartment advancing in the direction of insertion relative to the frame; and withdrawing the upper cap and the cannula from the user's body tissue, leaving the analyte sensor inserted into the user's body tissue and the electronics compartment mounted on the user's skin.

\* \* \* \* \*